United States Patent
Mironov et al.

(10) Patent No.: US 12,090,269 B2
(45) Date of Patent: Sep. 17, 2024

(54) AEROSOL-GENERATING SYSTEM HAVING A HEATER ASSEMBLY AND A CARTRIDGE FOR AN AEROSOL-GENERATING SYSTEM HAVING A FLUID PERMEABLE HEATER ASSEMBLY

(71) Applicant: Philip Morris Products S.A., Neuchatel (CH)

(72) Inventors: Oleg Mironov, Neuchatel (CH); Rui Nuno Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 18/166,190

(22) Filed: Feb. 8, 2023

(65) Prior Publication Data

US 2023/0191045 A1 Jun. 22, 2023

Related U.S. Application Data

(63) Continuation of application No. 17/081,615, filed on Oct. 27, 2020, now Pat. No. 11,602,602, which is a (Continued)

(30) Foreign Application Priority Data

Feb. 10, 2014 (EP) .................................. 14154553

(51) Int. Cl.
*A61M 15/00* (2006.01)
*A24F 40/42* (2020.01)
(Continued)

(52) U.S. Cl.
CPC ......... *A61M 15/0028* (2013.01); *A24F 40/42* (2020.01); *A24F 40/44* (2020.01); (Continued)

(58) Field of Classification Search
CPC ........ A24F 47/008; A24F 40/10; A24F 40/42; A24F 40/44; A24F 40/46; A24F 40/53; (Continued)

(56) References Cited

U.S. PATENT DOCUMENTS

| | | | |
|---|---|---|---|
| 4,922,901 A | 5/1990 | Brooks et al. |
| 4,947,874 A | 8/1990 | Brooks et al. |

(Continued)

FOREIGN PATENT DOCUMENTS

| | | | |
|---|---|---|---|
| CN | 1205849 A | 1/1999 |
| CN | 101116542 A | 2/2008 |

(Continued)

OTHER PUBLICATIONS

International Search Report and Written Opinion issued Jun. 9, 2015 in PCT/EP2014/077843, filed Dec. 15, 2014.

(Continued)

*Primary Examiner* — Hung D Nguyen
(74) *Attorney, Agent, or Firm* — Oblon, McClelland, Maier & Neustadt, L.L.P.

(57) ABSTRACT

A cartridge for an electrically operated aerosol-generating system is provided, the cartridge including: a liquid storage portion including a housing holding a liquid aerosol-forming substrate, the housing having an opening; and a fluid-permeable heater assembly including a plurality of electrically conductive filaments, the fluid-permeable heater assembly being fixed to the housing and extending across the opening of the housing. An aerosol-generating system, and a method of manufacture of a cartridge for an electrically operated aerosol-generating system, are also provided.

24 Claims, 17 Drawing Sheets

Related U.S. Application Data continuation of application No. 15/117,661, filed as application No. PCT/EP2014/077843 on Dec. 15, 2014, now Pat. No. 10,874,142.

(51) Int. Cl.

| | | |
|---|---|---|
| *A24F 40/44* | (2020.01) | |
| *A24F 40/46* | (2020.01) | |
| *A24F 40/53* | (2020.01) | |
| *A61M 11/00* | (2006.01) | |
| *A61M 11/04* | (2006.01) | |
| *A61M 15/06* | (2006.01) | |
| *B32B 3/26* | (2006.01) | |
| *B32B 5/02* | (2006.01) | |
| *B32B 27/06* | (2006.01) | |
| *B32B 27/12* | (2006.01) | |
| *B32B 27/28* | (2006.01) | |
| *H05B 3/14* | (2006.01) | |
| *H05B 3/34* | (2006.01) | |
| *A24F 40/10* | (2020.01) | |

(52) U.S. Cl.
CPC .............. *A24F 40/46* (2020.01); *A24F 40/53* (2020.01); *A61M 11/003* (2014.02); *A61M 11/042* (2014.02); *A61M 15/0021* (2014.02); *A61M 15/06* (2013.01); *B32B 3/266* (2013.01); *B32B 5/024* (2013.01); *B32B 27/06* (2013.01); *B32B 27/12* (2013.01); *B32B 27/281* (2013.01); *H05B 3/145* (2013.01); *H05B 3/34* (2013.01); *H05B 3/347* (2013.01); *A24F 40/10* (2020.01); *A61M 2205/8206* (2013.01); *A61M 2206/14* (2013.01); *B32B 2250/02* (2013.01); *B32B 2262/106* (2013.01); *B32B 2307/202* (2013.01); *B32B 2457/00* (2013.01); *H05B 2203/015* (2013.01); *H05B 2203/021* (2013.01)

(58) Field of Classification Search
CPC .......... A61M 15/0003; A61M 15/0021; A61M 15/0028; A61M 15/06; A61M 11/003; A61M 11/041; A61M 11/042; A61M 2205/8206; A61M 2206/14; H05B 3/0014; H05B 3/12; H05B 3/141; H05B 3/145; H05B 3/24; H05B 3/26; H05B 3/34; H05B 3/347; H05B 2203/015; H05B 2203/021; B32B 27/06; B32B 27/12; B32B 27/281; B32B 5/024; B32B 2250/02; B32B 3/266; B32B 2457/00; B32B 2307/202; B32B 2262/106
USPC ........ 392/386, 391, 394, 395; 131/273, 328, 131/329
See application file for complete search history.

(56) References Cited

U.S. PATENT DOCUMENTS

| | | | |
|---|---|---|---|
| 4,947,875 | A | 8/1990 | Brooks et al. |
| 5,060,671 | A | 10/1991 | Counts et al. |
| 5,408,574 | A | 4/1995 | Deevi et al. |
| 5,666,977 | A | 9/1997 | Higgins et al. |
| 9,004,073 | B2 | 4/2015 | Tucker et al. |
| 2003/0033055 | A1 | 2/2003 | Mcrae et al. |
| 2005/0268911 | A1 | 12/2005 | Cross et al. |
| 2008/0022999 | A1 | 1/2008 | Belcastro et al. |
| 2009/0220222 | A1 | 9/2009 | Rabin et al. |
| 2011/0226236 | A1 | 9/2011 | Buchberger |
| 2011/0265806 | A1 | 11/2011 | Alarcon et al. |
| 2011/0309157 | A1 | 12/2011 | Yang et al. |
| 2013/0081642 | A1 | 4/2013 | Safari |
| 2013/0087160 | A1 | 4/2013 | Gherghe |
| 2013/0213419 | A1 | 8/2013 | Tucker et al. |
| 2013/0312776 | A1 | 11/2013 | Newton |
| 2013/0319436 | A1 | 12/2013 | Liu |
| 2014/0000638 | A1 | 1/2014 | Sebastian et al. |
| 2014/0060554 | A1 | 3/2014 | Collett et al. |
| 2014/0202454 | A1 | 7/2014 | Buchberger |
| 2014/0305454 | A1 | 10/2014 | Rinker et al. |
| 2015/0053214 | A1 | 2/2015 | Alarcon et al. |
| 2015/0059779 | A1 | 3/2015 | Alarcon et al. |
| 2017/0035109 | A1 | 2/2017 | Liu |

FOREIGN PATENT DOCUMENTS

| | | |
|---|---|---|
| CN | 102264420 A | 11/2011 |
| CN | 102573968 A | 7/2012 |
| CN | 102861694 A | 1/2013 |
| CN | 202749479 U | 2/2013 |
| CN | 102970885 A | 3/2013 |
| CN | 103504480 A | 1/2014 |
| CN | 103533684 A | 1/2014 |
| CN | 203369386 U | 1/2014 |
| CN | 203986095 U | 12/2014 |
| CN | 203986096 U | 12/2014 |
| DE | 20 2013 100 606 U1 | 4/2013 |
| EA | 201100197 A1 | 3/2012 |
| EP | 2 574 247 A1 | 4/2013 |
| EP | 2 633 875 A2 | 9/2013 |
| JP | 2000-41654 | 2/2000 |
| JP | 2012-506263 A | 3/2012 |
| KR | 10-2008-0059567 A | 6/2008 |
| KR | 10-2013-0046826 A | 5/2013 |
| RU | 110 608 U1 | 11/2011 |
| RU | 132 318 U1 | 9/2013 |
| TW | 201325481 A1 | 7/2013 |
| WO | WO 03/103387 A2 | 12/2003 |
| WO | WO 2008/108889 A1 | 9/2008 |
| WO | WO 2010/045671 A1 | 4/2010 |
| WO | WO 2011/009920 A1 | 1/2011 |
| WO | WO 2011/042212 A1 | 4/2011 |
| WO | WO 2011/045672 A1 | 4/2011 |
| WO | WO 2013/013808 A1 | 1/2013 |
| WO | WO 2013/045582 A2 | 4/2013 |
| WO | WO 2013/083634 A1 | 6/2013 |
| WO | WO 2013/126777 A2 | 8/2013 |
| WO | WO 2013/148810 A1 | 10/2013 |
| WO | WO 2014/012906 A1 | 1/2014 |
| WO | WO 2015/161459 A1 | 10/2015 |

OTHER PUBLICATIONS

Singaporean Office Action issued Jul. 17, 2017 in Singaporean Patent Application No. 11201605890Y.
Combined Taiwanese Office Action and Search Report issued on Jun. 29, 2018 in Patent Application No. 104103824 (submitting English translation only), 10 pages.
Combined Chinese Office Action and Search Report issued Sep. 4, 2018 in Chinese Patent Application No. 201480074316.3 (submitting English translation only), 9 pages.
Office Action issued Nov. 15, 2018 in Russian Patent Application No. 2016136343, 11 pages (with English translation and English translation of categories of cited documents).
Combined Office Action and Search Report issued May 15, 2019 in Chinese Patent Application No. 201480074316.3, 18 pages (with English translation).
Chinese Office Action mailed on Oct. 3, 2019 in corresponding Chinese Patent Application No. 2016-551319, (5 pages).
Japanese Office Action with English translation mailed on Oct. 3, 2019 in corresponding Japanese Patent Application No. 2016-551319 (17 pages).
Kanthal (alloy), Wikipedia, Retrieved from the internet: https://en.wikipedia.org/w/index.php?title=Kanthal_(alloy)&oldid=920685181, Oct. 11, 2019, 2 pages.
"Kynol Activated Carbon Fibers & Textiles", Kynol Europa GmbH, 2012, cited in the opposition Jan. 8, 2020, 3 pages.

(56) References Cited

OTHER PUBLICATIONS

Cambridge English Dictionary definition of opening, Retrieved from the internet: https://dictionary.cambridge.org/dictionary/english/opening, retrieved on Jan. 4, 2021, 1 page.
Combined Taiwanese Office Action and Search Report issued Jun. 25, 2021 in Taiwanese Patent Application No. 104103824 (with English translation), 13 pages.
Korean Office Action issued Jun. 28, 2022 in Korean Patent Application No. 10-2022-7007988 (with English translation), 11 pages.
Combined Russian Office Action and Search Report issued Oct. 6, 2022, in corresponding Russian Patent Application No. 2019118674 (with English Translation), 14 pages.
Office Action mailed on Oct. 26, 2022 in Chinese Patent Application No. 202010100767.7 filed on Dec. 15, 2014, therein (with English translation, total 22 pages).
Search Report mailed on Oct. 26, 2022 in Chinese Patent Application No. 202010100767.7 filed on Dec. 15, 2014, therein (with English translation, total 7 pages).
Korean Notice of Allowance issued Nov. 27, 2023 in Korean Patent Application No. 10-2023-7010180 (With English Translation), 4 pages.

AEROSOL-GENERATING SYSTEM HAVING A HEATER ASSEMBLY AND A CARTRIDGE FOR AN AEROSOL-GENERATING SYSTEM HAVING A FLUID PERMEABLE HEATER ASSEMBLY

CROSS-REFERENCE TO RELATED APPLICATIONS

This application is a continuation of and claims benefit under 35 U.S.C. § 120 from U.S. application Ser. No. 17/081,615, filed on Oct. 27, 2020, which is a continuation of and claims benefit under 35 U.S.C. § 120 from U.S. application Ser. No. 15/117,661, filed Aug. 9, 2016 (now U.S. Pat. No. 10,874,142), which is a U.S. National Stage application of PCT/EP2014/077843, filed Dec. 15, 2014, and claims the benefit of priority under 35 U.S.C. § 119 from EP 14154553.3, filed Feb. 10, 2014, the entire contents of each of which are incorporated herein by reference.

The present invention relates to aerosol-generating systems that comprise a heater assembly that is suitable for vapourising a liquid. In particular, the invention relates to handheld aerosol-generating systems, such as electrically operated smoking systems.

One type of aerosol-generating system is an electrically operated smoking system. Handheld electrically operated smoking systems consisting of a device portion comprising a battery and control electronics, and a cartridge portion comprising a supply of aerosol-forming substrate, and an electrically operated vapouriser, are known. A cartridge comprising both a supply of aerosol-forming substrate and a vapouriser is sometimes referred to as a "cartomiser". The vapouriser typically comprises a coil of heater wire wound around an elongate wick soaked in liquid aerosol-forming substrate. The cartridge portion typically comprises not only the supply of aerosol-forming substrate and an electrically operated vapouriser, but also a mouthpiece, which the user sucks on in use to draw aerosol into their mouth.

However, this arrangement has the drawback that the cartridges are relatively expensive to produce. This is because manufacturing the wick and coil assembly is difficult. Also, the electrical contacts between the coil of heater wire and the electrical contacts through which electrical current is delivered from the device portion must be delicately handled during manufacture. Furthermore, these cartridges include a mouthpiece portion in order to protect the delicate wick and coil assembly during transport. But the inclusion of a complete and robust mouthpiece in each cartridge means that each cartridge has a high material cost.

It would be desirable to provide a heater assembly suitable for an aerosol-generating system, such as a handheld electrically operated smoking system, that is inexpensive to produce and is robust. It would be further desirable to provide a heater assembly that is more efficient than prior heater assemblies in aerosol-generating systems.

In a first aspect there is provided an aerosol-generating system comprising:
a liquid storage portion comprising a housing holding a liquid aerosol-forming substrate, the housing having an opening; and
a fluid permeable heater assembly comprising a plurality of electrically conductive filaments, wherein the fluid permeable heater assembly is fixed to the housing and extends across the opening of the housing.

The provision of a heater assembly that extends across an opening of a liquid storage portion allows for a robust construction that is relatively simple to manufacture. This arrangement allows for a large contact area between the heater assembly and liquid aerosol-forming substrate. The housing may be a rigid housing. As used herein "rigid housing" means a housing that is self-supporting. The rigid housing of the liquid storage portion preferably provides mechanical support to the heater assembly. The heater assembly may be substantially flat allowing for simple manufacture. As used herein, "substantially flat" means formed initially in a single plane and not wrapped around or other conformed to fit a curved or other non-planar shape. Geometrically, the term "substantially flat" electrically conductive filament arrangement is used to refer to an electrically conductive filament arrangement that is in the form of a substantially two dimensional topological manifold. Thus, the substantially flat electrically conductive filament arrangement extends in two dimensions along a surface substantially more than in a third dimension. In particular, the dimensions of the substantially flat filament arrangement in the two dimensions within the surface is at least 5 times larger than in the third dimension, normal to the surface. An example of a substantially flat filament arrangement is a structure between two substantially imaginary parallel surfaces, wherein the distance between these two imaginary surfaces is substantially smaller than the extension within the surfaces. In some embodiments, the substantially flat filament arrangement is planar. In other embodiments, the substantially flat filament arrangement is curved along one or more dimensions, for example forming a dome shape or bridge shape.

The term "filament" is used throughout the specification to refer to an electrical path arranged between two electrical contacts. A filament may arbitrarily branch off and diverge into several paths or filaments, respectively, or may converge from several electrical paths into one path. A filament may have a round, square, flat or any other form of cross-section. A filament may be arranged in a straight or curved manner.

The term "filament arrangement" is used throughout the specification to refer to an arrangement of one or preferably a plurality of filaments. The filament arrangement may be an array of filaments, for example arranged parallel to each other. Preferably, the filaments may form a mesh. The mesh may be woven or non-woven.

A flat heater assembly can be easily handled during manufacture and provides for a robust construction.

The system may advantageously comprise a device and a cartridge that is removably coupled to the device, wherein the liquid storage portion and heater assembly are provided in the cartridge and the device comprises a power supply. The cartridge may be manufactured at low cost, in a reliable and repeatable fashion. As used herein, the cartridge being "removably coupled" to the device means that the cartridge and device can be coupled and uncoupled from one another without significantly damaging either the device or the cartridge.

The system may be an electrically operated smoking system.

The electrically conductive filaments may lie in a single plane. A planar heater assembly can be easily handled during manufacture and provides for a robust construction.

The electrically conductive filaments may define interstices between the filaments and the interstices may have a width of between 10 µm and 100 µm. Preferably the filaments give rise to capillary action in the interstices, so that in use, liquid to be vapourised is drawn into the interstices, increasing the contact area between the heater assembly and the liquid.

The electrically conductive filaments may form a mesh of size between 160 and 600 Mesh US (±10%) (i.e. between 160 and 600 filaments per inch (±10%)). The width of the interstices is preferably between 75 μm and 25 μm. The percentage of open area of the mesh, which is the ratio of the area of the interstices to the total area of the mesh is preferably between 25% and 56%. The mesh may be formed using different types of weave or lattice structures. Alternatively, the electrically conductive filaments consist of an array of filaments arranged parallel to one another.

The mesh, array or fabric of electrically conductive filaments may also be characterised by its ability to retain liquid, as is well understood in the art.

The electrically conductive filaments may have a diameter of between 10 μm and 100 μm, preferably between 8 μm and 50 μm, and more preferably between 8 μm and 39 μm. The filaments may have a round cross section or may have a flattened cross-section.

The area of the mesh, array or fabric of electrically conductive filaments may be small, preferably less than or equal to 25 mm², allowing it to be incorporated in to a handheld system. The mesh, array or fabric of electrically conductive filaments may, for example, be rectangular and have dimensions of 5 mm by 2 mm. Preferably, the mesh or array of electrically conductive filaments covers an area of between 10% and 50% of the area of the heater assembly. More preferably, the mesh or array of electrically conductive filaments covers an area of between 15% and 25% of the area of the heater assembly. Sizing of the mesh, array or fabric of electrically conductive filaments 10% and 50% of the area, or less or equal than 25 mm2, reduces the amount of total power required to heat the mesh, array or fabric of electrically conductive filaments while still ensuring sufficient contact of the mesh, array or fabric of electrically conductive filaments to the liquid provided one or more capillary materials to be volatilized.

The heater filaments may be formed by etching a sheet material, such as a foil. This may be particularly advantageous when the heater assembly comprises an array of parallel filaments. If the heater assembly comprises a mesh or fabric of filaments, the filaments may be individually formed and knitted together. Alternatively, the heater filaments may be stamped from electrically conductive foil, as for example stainless steel.

The filaments of the heater assembly may be formed from any material with suitable electrical properties. Suitable materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation. The filaments may be coated with one or more insulators. Preferred materials for the electrically conductive filaments are 304, 316, 304L, 316L stainless steel, and graphite. Additionally, the electrically conductive filament arrangement may comprise combinations of the above materials. A combination of materials may be used to improve the control of the resistance of the substantially flat filament arrangement. For example, materials with a high intrinsic resistance may be combined with materials with a low intrinsic resistance. This may be advantageous if one of the materials is more beneficial from other perspectives, for example price, machinability or other physical and chemical parameters. Advantageously, a substantially flat filament arrangement with increased resistance reduces parasitic losses. Advantageously, high resistivity heaters allows more efficient use of battery energy. The battery energy is proportionally divided between the energy lost on the printed circuit board and the contacts and energy delivered to the electrically conductive filament arrangement. Thus the energy available for the electrically conductive filament arrangement in the heater is higher the higher the resistance of the electrically conductive filament arrangement.

In an exemplary embodiment, a substantially flat filament arrangement may be constructed from two types of metal wires that are formed into a wire mesh. In such an embodiment, preferably, high resistive wires are oriented in the direction of the flow of electric current, for example, wires made from a nickel chromium alloy. Accordingly, in this embodiment low resistive wires are arranged substantially perpendicular to the wires with high electrical resistance. For example, the low resistive wires may be stainless steel wires. Advantageously, the relatively cheaper low resistance wires form the support for the wires with high electrical resistance. In addition, wires with high electrical resistance typically are less malleable than stainless steel wires and can thus not be manufactured easily into thin wires. Therefore, in such an advantageous embodiment of the invention, the relatively thick wires with high electrical resistance are combined with thin stainless steel wires of low electrical resistance with the added benefit that the thinner stainless steel wires improve the wetting of the substantially flat filament arrangement through the increased capillary forces.

Alternatively, the electrically conductive filament arrangement may be formed of carbon thread textile. Carbon thread textile has the advantage that it is typically more cost efficient than metallic heaters with high resistivity. Further, a carbon thread textile is typically more flexible than a metallic mesh. Another advantage is that the contact between a carbon thread textile and a transport medium like a high release material can be well preserved during construction of the fluid permeable heater assembly.

A reliable contact between the fluid permeable heater assembly and a transport medium, like for example a capillary transport medium such as a wick made from fibres or a porous ceramic material, improves the constant wetting of the fluid permeable heater assembly. This advantageously reduces the risk of overheating of the electrically conductive filament arrangement and inadvertent thermal decomposition of the liquid.

The heater assembly may comprise an electrically insulating substrate on which the filaments are supported. The electrically insulating substrate may comprise any suitable material, and is preferably a material that is able to tolerate high temperatures (in excess of 300 degrees Celsius) and rapid temperature changes. An example of a suitable material is a polyimide film, such as Kapton®. The electrically insulating substrate may have an aperture formed in it, with the electrically conductive filaments extending across the aperture. The heater assembly may comprise electrical contacts connected to the electrically conductive filaments. For example, the electrical contacts may be glued, welded or mechanically clamped to the electrically conductive filament arrangement. Alternatively the electrically conductive filament arrangement may be printed on the electrically insulating substrate, for example using metallic inks. In such an arrangement, preferably, the electrically insulating substrate is a porous material, such that the electrically conductive filament arrangement can be directly applied to the surface of the porous material. Preferably, in such an embodiment the porosity of the substrate functions as the "opening" of the electrically insulating substrate through which a liquid may be drawn towards the electrically conductive filament arrangement.

The electrical resistance of the mesh, array or fabric of electrically conductive filaments of the heater element is preferably between 0.3 Ohms and 4 Ohms. More preferably, the electrical resistance of the mesh, array or fabric of electrically conductive filaments is between 0.5 Ohms and 3 Ohms, and more preferably about 1 Ohm. The electrical resistance of the mesh, array or fabric of electrically conductive filaments is preferably at least an order of magnitude, and more preferably at least two orders of magnitude, greater than the electrical resistance of the contact portions. This ensures that the heat generated by passing current through the heater element is localised to the mesh or array of electrically conductive filaments. It is advantageous to have a low overall resistance for the heater element if the system is powered by a battery. A low resistance, high current system allows for the delivery of high power to the heater element. This allows the heater element to heat the electrically conductive filaments to a desired temperature quickly.

The first and second electrically conductive contact portions may be fixed directly to the electrically conductive filaments. The contact portions may be positioned between the electrically conductive filaments and the electrically insulating substrate. For example, the contact portions may be formed from a copper foil that is plated onto the insulating substrate. The contact portions may also bond more readily with the filaments than the insulating substrate would.

Alternatively, the first and second electrically conductive contact portions may be integral with the electrically conductive filaments. For example, the heater element may be formed by etching a conductive sheet to provide a plurality of filaments between two contact portions.

The heater assembly may comprise at least one filament made from a first material and at least one filament made from a second material different from the first material. This may be beneficial for electrical or mechanical reasons. For example, one or more of the filaments may be formed from a material having a resistance that varies significantly with temperature, such as an iron aluminium alloy. This allows a measure of resistance of the filaments to be used to determine temperature or changes in temperature. This can be used in a puff detection system and for controlling heater temperature to keep it within a desired temperature range. Sudden changes in temperature may also be used as a means to detect changes in air flow past the heater assembly resulting from a user puffing on the system.

The housing of the liquid storage portion advantageously contains a capillary material. A capillary material is a material that actively conveys liquid from one end of the material to another. The capillary material is advantageously oriented in the housing to convey liquid to the heater assembly.

The capillary material may have a fibrous or spongy structure. The capillary material preferably comprises a bundle of capillaries. For example, the capillary material may comprise a plurality of fibres or threads or other fine bore tubes. The fibres or threads may be generally aligned to convey liquid to the heater. Alternatively, the capillary material may comprise sponge-like or foam-like material. The structure of the capillary material forms a plurality of small bores or tubes, through which the liquid can be transported by capillary action. The capillary material may comprise any suitable material or combination of materials. Examples of suitable materials are a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity and porosity so as to be used with different liquid physical properties. The liquid has physical properties, including but not limited to viscosity, surface tension, density, thermal conductivity, boiling point and vapour pressure, which allow the liquid to be transported through the capillary device by capillary action.

The capillary material may be in contact with the electrically conductive filaments. The capillary material may extend into interstices between the filaments. The heater assembly may draw liquid aerosol-forming substrate into the interstices by capillary action. The capillary material may be in contact with the electrically conductive filaments over substantially the entire extent of the aperture. In one embodiment the capillary material in contact with the electrically conductive filament arrangement may be a filamentary wick. Preferably, the filamentary wick has a first section and a second section, wherein the first section is arranged substantially perpendicular to the electrically conductive filament arrangement, reaching into the liquid storage portion of the cartridge. Preferably, the second section of the filamentary wick is arranged substantially in parallel to the electrically conductive filament arrangement. Preferably, the filaments of the filamentary wick are continuous from the first section of the filamentary wick to the second section of the filamentary wick. This allows a quick transport of the liquid towards the electrically conductive filament arrangement through the first section of the filamentary wick and, at the same time, a quick distribution across the electrically conductive filament arrangement through the second section of the filamentary wick. This allows advantageously a continuous wetting of the entire the electrically conductive filament arrangement. A continuous wetting can avoid overheating and prevent the inadvertent decomposition of the liquid due to the overheating.

Preferably, the electrically conductive filament arrangement comprises at least several filaments made of alloys or coated with films which are sensitive to presence of liquid such as water. This allows the detection of wetting of the electrically conductive filament arrangement, for example by connecting the sensitive wires to a circuit that monitors electrical resistance of the wires and prevent the heater from working or reduce an electrical current in case of detection of dry interface. This advantageously increases the safety of aerosol generating system. In one embodiment, the filaments that are used for detection of the wetting are stainless steel wires that are coated with Indium nitride (InN) or aluminium oxide (Al2O3) films. In use, a liquid like water depletes electrons from such film surfaces and preserves high electrical resistivity of the film up to the moment when film surface becomes dry. Then the resistivity drops rapidly. The drop in resistivity is be detected by the connected electronic circuit.

Advantageously, the heater assembly and the capillary material may be sized to have approximately the same area. As used here, approximately means between that the heater assembly may be between 0-15% larger than the capillary material. The shape of the heater assembly may also be similar to the shape of the capillary material such that the assembly and the material substantially overlap. When the assembly and the material are substantially similar in size and shape, manufacturing can be simplified and the robustness of the manufacturing process improved. As discussed below, the capillary material may include two or more capillary materials including one or more layers of the capillary material directly in contact with the mesh, array or fabric of electrically conductive filaments of the heater assembly in order to promote aerosol generation. The capillary materials may include materials described herein.

At least one of the capillary materials may be of sufficient volume in order to ensure that a minimal amount of liquid is present in said capillary material to prevent "dry heating", which occurs if insufficient liquid is provided to the capillary material in contact with the mesh, array or fabric of electrically conductive filaments. A minimum volume of said capillary material may be provided in order to allow for between 20-40 puffs by the user. An average volume of liquid volatilized during a puff of a length between 1-4 seconds is typically between 1-4 mg of liquid. Thus, providing at least one capillary material having a volume to retain between 20-160 mg of the liquid comprising the liquid-forming substrate may prevent the dry heating.

The housing may contain two or more different capillary materials, wherein a first capillary material, in contact with the heater element, has a higher thermal decomposition temperature and a second capillary material, in contact with the first capillary material but not in contact with the heater element has a lower thermal decomposition temperature. The first capillary material effectively acts as a spacer separating the heater element from the second capillary material so that the second capillary material is not exposed to temperatures above its thermal decomposition temperature. As used herein, "thermal decomposition temperature" means the temperature at which a material begins to decompose and lose mass by generation of gaseous by products. The second capillary material may advantageously occupy a greater volume than the first capillary material and may hold more aerosol-forming substrate that the first capillary material. The second capillary material may have superior wicking performance to the first capillary material. The second capillary material may be cheaper than the first capillary material. The second capillary material may be polypropylene.

The first capillary material may separate the heater assembly from the second capillary material by a distance of at least 1.5 mm, and preferably between 1.5 mm and 2 mm in order to provide a sufficient temperature drop across the first capillary material.

The liquid storage portion may be positioned on a first side of the electrically conductive filaments and an airflow channel positioned on an opposite side of the electrically conductive filaments to the liquid storage portion, such that air flow past the electrically conductive filaments entrains vapourised liquid aerosol-forming substrate.

In addition to the electrical heater assembly that is located in close proximity or in contact to the liquid transport medium, the aerosol-generating system may comprise at least one further electrical heater assembly in operational relationship with the liquid storage portion. A further electrical heater assembly in operational relationship with the liquid storage portion may increase the depletion of the liquid from liquid storage portion. This is particularly advantageous where the liquid storage portion comprises a high retention medium storing the liquid. It is advantageous to use a high retention medium to store liquid in the liquid storage portion. For example, the use a high retention medium reduces the risk of spill. In case of failure or cracks of the housing of the cartridge spilled liquid could lead to unintended contact with active electrical components and biological tissues. However, as the liquid is attracted by wettability forces to the high retention medium surface, a substantial loss of liquid is less likely if compared to free liquid filled tanks in case of mechanical cracks in the cartridge housing. However, as the high retention medium will intrinsically retain at least some portion of the liquid, which in turn is not available for aerosolization. Advantageously, the provision of additional heating assemblies increases the ratio of the depletion of the liquid storage portion, that is, the ratio between the amount of liquid removed from the liquid storage portion and the amount of liquid that cannot be removed from the liquid storage portion.

Preferably, the further electrical heater assembly is located close to the areas of the high retention medium that are less likely to be depleted by the primary electrical heater assembly, for example, the most areas of the high retention medium that are most distant from the first electrical heater assembly. Preferably, the further electrical heater assembly is located in the bottom wall of the housing, that is, the wall that is opposite of the electrical heater assembly. Alternatively or in addition, the further electrical heater assembly is located at a side wall of the housing.

Preferably, the further electrical heater assembly is controlled to be activated only as needed, for example when a reduction of the liquid flow is detected. For example, the further electrical heater assembly may be activated when a reduction in the wetting of the first electrical heater assembly is detected.

Alternatively or in addition, the housing has internally a non-cylindrical, for example a conical form, such that the wider section of the internal non-cylindrical form is directed towards the electrical heater assembly and the internal smaller section extends into an opposite direction. This allows for an increase of the relevance of the gravitational forces acting on the liquid to advance the liquid towards the electrical heater assembly, in particular where the aerosol-generating system is in a substantially horizontal orientation. A horizontal orientation is an orientation in which the electrical heater assembly is substantially on the same vertical level as the liquid storage portion. This horizontal orientation is typical during the use of the aerosol-generating system.

Alternatively or in addition, the cartridge comprising the electrical heater assembly and the housing is arranged in the aerosol-generating system such that electrical heater assembly is arranged across the opening of the housing on the side of the liquid storage portion that is distant from the mouthpiece of the aerosol-generating system. This may be beneficial for the flow path of the aerosol within the aerosol generating system. For example, in a vertical arrangement of the aerosol generating system the mouthpiece is on the top and the housing is arranged up-side down, that is, the liquid is arranged above the electrical heater assembly. In such an embodiment, capillary forces to advance the liquid towards the electrical heater assembly are be assisted by the gravitational forces, instead of having to overcome the gravitational forces.

Preferably, the housing comprises two elements, wherein a first element is a cap and a second element is a tank, wherein the cap closes the tank. Preferably, according to the invention, the cap comprises or is in close contact with the heater assembly. Preferably, the tank comprises the liquid, and where present the first capillary material or both first and second capillary materials. Preferably, the cap material is made from a material with a high thermal decomposition temperature, such as for example polyetheretherketone (PEEK) or Kapton®. Preferably, the cap has a size sufficient to distance the tank from the heater assembly by a distance of at least 1.5 mm, and preferably between 1.5 mm and 2 mm in order to provide a sufficient temperature drop across the cap. Advantageously, in such an embodiment, the tank material can be made from a more cost efficient material with a lower thermal decomposition temperature, such as for example polyethylene or polypropylene.

An air inlet of the for example be arranged in a main housing of the system. Ambient air is directed into the system, passes the heating element at the distal end of the cartridge and entrains an aerosol caused by heating the aerosol-forming substrate in the cartridge. The aerosol containing air may then be guided along the cartridge between a cartridge housing and a main housing to the downstream end of the system, where it is mixed with ambient air from the further flow route (either before or upon reaching the downstream end).

An inlet opening of the second channel arranged in a region of a distal end of a cartridge housing may also be provided in an alternative system where a heating element is arranged at a proximal end of the cartridge. The second flow route may not only pass outside of the cartridge but also through the cartridge. Ambient air then enters the cartridge at a semi-open wall of the cartridge, passes through the cartridge and leaves the cartridge by passing though the heating element arranged at the proximal end of the cartridge. Thereby, ambient air may pass through the aerosol-forming substrate or through one or several channels arranged in a solid aerosol-forming substrate such that ambient air does not pass through the substrate itself but in the channels next to the substrate.

For allowing ambient air to enter a cartridge, a wall of the cartridge housing, preferably a wall opposite the heating element, preferably a bottom wall, is provided with at least one semi-open inlet. The semi-open inlet allows air to enter the cartridge but no air or liquid to leave the cartridge through the semi-open inlet. A semi-open inlet may for example be a semi-permeable membrane, permeable in one direction only for air but is air- and liquid-tight in the opposite direction. A semi-open inlet may for example also be a one-way valve. Preferably the semi-open inlets allow air to pass through the inlet only if specific conditions are met, for example a minimum depression in the cartridge or a volume of air passing through the valve or membrane.

Such one-way valves may, for example, be commercially available valves, such as for example used in medical devices, for example LMS Mediflow One-Way, LMS Sure-Flow One-Way or LMS Check Valves (crosses membranes). Suitable membranes to be used for a cartridge having an airflow passing through the cartridge, are for example vented membranes as used in medical devices, for example Qosina Ref. 11066, vented cap with hydrophobic filter or valves as used in baby bottles. Such valves and membranes may be made of any material suitable for applications in electrically heated smoking systems. Materials suitable for medical devices and FDA approved materials may be used; for example Graphene having very high mechanical resistance and thermal stability within a large range of temperatures. Preferably, valves are made of soft resilient material for supporting a liquid-tight incorporation of the one or several valves into a wall of the container housing.

Letting ambient air pass through the substrate supports an aerosolization of the aerosol-forming substrate. During puffing, a depression occurs in the cartridge, which may activate the semi-open inlets. Ambient air then passes the cartridge, preferably a high retention or high release material (HRM) or a liquid, and crosses the heating element, thereby creating and sustaining aerosolization of the liquid, when the heating element sufficiently heats the liquid. In addition, due to the depression caused during puffing, a supply of liquid in a transport material such as a capillary material to the heating element may be limited. An ambient airflow through the cartridge may equalize pressure differences within the cartridge and thereby support an unhindered capillary action towards the heating element.

A semi-open inlet may, in addition, or alternatively also be provided in one or several side walls of the cartridge housing. Semi-open inlets in side walls provide a lateral airflow into the cartridge towards the open top end of the cartridge housing, where the heating element is arranged. Preferably, lateral airflows pass through the aerosol-forming substrate.

The system may further comprise electric circuitry connected to the heater assembly and to an electrical power source, the electric circuitry configured to monitor the electrical resistance of the heater assembly or of one or more filaments of the heater assembly, and to control the supply of power to the heater assembly dependent on the electrical resistance of the heater assembly or the one or more filaments.

The electric circuitry may comprise a microprocessor, which may be a programmable microprocessor. The electric circuitry may comprise further electronic components. The electric circuitry may be configured to regulate a supply of power to the heater assembly. Power may be supplied to the heater assembly continuously following activation of the system or may be supplied intermittently, such as on a puff-by-puff basis. The power may be supplied to the heater assembly in the form of pulses of electrical current.

The system advantageously comprises a power supply, typically a battery, within the main body of the housing. As an alternative, the power supply may be another form of charge storage device such as a capacitor. The power supply may require recharging and may have a capacity that allows for the storage of enough energy for one or more smoking experiences; for example, the power supply may have sufficient capacity to allow for the continuous generation of aerosol for a period of around six minutes or for a period that is a multiple of six minutes. In another example, the power supply may have sufficient capacity to allow for a predetermined number of puffs or discrete activations of the heater assembly.

Preferably, the aerosol generating system comprises a housing. Preferably, the housing is elongate. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

Preferably, the aerosol-generating system is portable. The aerosol-generating system may have a size comparable to a conventional cigar or cigarette. The smoking system may have a total length between approximately 30 mm and approximately 150 mm. The smoking system may have an external diameter between approximately 5 mm and approximately 30 mm.

The aerosol-forming substrate is a substrate capable of releasing volatile compounds that can form an aerosol. The volatile compounds may be released by heating the aerosol-forming substrate.

The aerosol-forming substrate may comprise plant-based material. The aerosol-forming substrate may comprise tobacco. The aerosol-forming substrate may comprise a tobacco-containing material containing volatile tobacco flavour compounds, which are released from the aerosol-forming substrate upon heating. The aerosol-forming substrate may alternatively comprise a non-tobacco-containing material. The aerosol-forming substrate may comprise homogenised plant-based material. The aerosol-forming substrate may comprise homogenised tobacco material. The aerosol-forming substrate may comprise at least one aerosol-former. The aerosol-forming substrate may comprise other additives and ingredients, such as flavourants.

In a second aspect, there is provided a cartridge for use in an electrically operated aerosol-generating system, comprising:
 a liquid storage portion comprising a housing holding a liquid aerosol-forming substrate, the housing having an opening; and
 a fluid permeable heater assembly comprising a plurality of electrically conductive filaments, wherein the fluid permeable heater assembly extends across the opening of the housing of the liquid storage portion.

A cartridge with this construction may be made robust, reliable and at low cost. The heater assembly may be substantially flat, without the need for any winding of a heater wire around a capillary wick.

The electrically conductive filaments may lie in a single plane. A planar heater assembly can be easily handled during manufacture and provides for a robust construction.

The electrically conductive filaments may define interstices between the filaments and the interstices may have a width of between 10 μm and 100 μm. Preferably the filaments give rise to capillary action in the interstices, so that in use, liquid to be vapourised is drawn into the interstices, increasing the contact area between the heater assembly and the liquid.

The electrically conductive filaments may form a mesh of size between 160 and 600 Mesh US (±10%) (i.e. between 160 and 600 filaments per inch (±10%)). The width of the interstices is preferably between 75 μm and 25 μm. The percentage of open area of the mesh, which is the ration of the area of the interstices to the total area of the mesh is preferably between 25 and 56%. The mesh may be formed using different types of weave or lattice structures. Alternatively, the electrically conductive filaments consist of an array of filaments arranged parallel to one another.

The electrically conductive filaments may have a diameter of between 10 μm and 100 μm, preferably between 8 μm and 50 μm, and more preferably between 8 μm and 39 μm. The filaments may have a round cross section or may have a flattened cross-section. The heater filaments may be formed by etching a sheet material, such as a foil. This may be particularly advantageous when the heater assembly comprises an array of parallel filaments. If the heater assembly comprises a mesh or fabric of filaments, the filaments may be individually formed and knitted together.

The area of the mesh, array or fabric of electrically conductive filaments may be small, preferably less than or equal to 25 mm$^2$, allowing it to be incorporated in to a handheld system. The mesh, array or fabric of electrically conductive filaments may, for example, be rectangular and have dimensions of 5 mm by 2 mm. Preferably, the mesh or array of electrically conductive filaments covers an area of between 10% and 50% of the area of the heater assembly. More preferably, the mesh or array of electrically conductive filaments covers an area of between 15 and 25% of the area of the heater assembly.

The electrically conductive filaments may comprise any suitable electrically conductive material. Preferred materials for the electrically conductive filaments are 304, 316, 304L, 316L stainless steel, and graphite.

The electrical resistance of the mesh, array or fabric of electrically conductive filaments of the heater element is preferably between 0.3 and 4 Ohms. More preferably, the electrical resistance of the mesh, array or fabric of electrically conductive filaments is between 0.5 and 3 Ohms, and more preferably about 1 Ohm. The electrical resistance of the mesh, array or fabric of electrically conductive filaments is preferably at least an order of magnitude, and more preferably at least two orders of magnitude, greater than the electrical resistance of the contact portions.

The housing of the liquid storage portion may contain a capillary material, as described in relation to the first aspect. The capillary material may be oriented in the housing to convey liquid to the heater assembly. The capillary material may be in contact with the heater assembly. The capillary material may extend into interstices between the filaments.

As described in relation to the first aspect, the housing may contain two or more different capillary materials, wherein a first capillary material, in contact with the heater element, has a higher thermal decomposition temperature and a second capillary material, in contact with the first capillary material but not in contact with the heater element has a lower thermal decomposition temperature. The first capillary material may separate the heater assembly from the second capillary material by a distance of at least 1.5 mm, and preferably between 1.5 and 2 mm in order to provide a sufficient temperature drop across the first capillary material.

As described in relation to the first aspect, the heater assembly may comprise at least one filament made from a first material and at least one filament made from a second material different from the first material.

The heater assembly may comprise an electrically insulating substrate on which the filaments are supported, the filaments extending across an aperture formed in the substrate. The electrically insulating substrate may comprise any suitable material, and is preferably a material that is able to tolerate high temperatures (in excess of 300° C.) and rapid temperature changes. An example of a suitable material is a polyimide film, such as Kapton®.

The heater assembly may comprise an electrically conductive contact in contact with a plurality of the filaments. The electrically conductive contact may be provided between the housing of the liquid storage portion and the electrically insulating substrate. The electrically conductive contact may be provided between the filaments and the electrically insulating substrate. An aperture may be formed in the electrically insulating layer, and the cartridge may comprise two electrically conductive contacts positioned on opposite sides on the aperture to one another.

Advantageously, the electrically conductive contact is accessible from an exterior of the cartridge. The heater assembly may extend in a lateral plane and the electrically conductive contact may extend laterally beyond the housing of the liquid storage portion. The cartridge may then be configured to be inserted into an aerosol-generating device in a direction orthogonal to the lateral plane, bringing the electrically conductive contact into contact with an electrical contact on the device.

The housing of the liquid storage portion may be substantially cylindrical, wherein the opening is at one end of the cylinder. The housing of the liquid storage portion may have a substantially circular cross section.

The heater assembly is advantageously covered by a removable cover or seal prior to use. The cover or seal may protect the substrate from degradation during storage and transport.

In a preferred embodiment the cartridge does not comprise an electrical power source.

In a third aspect, there is provided a method of manufacture of a cartridge for use in an electrically operated aerosol-generating system, comprising:

- providing a liquid storage portion comprising a housing having an opening;
- filling the liquid storage portion with liquid aerosol-forming substrate; and
- fixing a fluid permeable heater assembly comprising a plurality of electrically conductive filaments to the liquid storage portion, wherein the fluid permeable heater assembly extends across the opening of the housing of the liquid storage portion.

The step of filling the liquid storage portion may be performed before or after the step of fixing the heater assembly to the liquid storage portion.

The step of fixing may, for example, comprise heat sealing, gluing or welding the heater assembly to the liquid storage portion. The liquid storage portion may contain a capillary material.

Features described in relation to one aspect may equally be applied to other aspects of the invention. In particular features described in relation to the first aspect may equally be applied to the second aspect and the third aspect.

As used herein, "electrically conductive" means formed from a material having a resistivity of $1\times10^{-4}$ Ωm, or less. As used herein, "electrically insulating" means formed from a material having a resistivity of $1\times10^{4}$ Ωm or more. As used herein "fluid permeable" in relation to a heater assembly means that the aerosol-forming substrate, in a gaseous phase and possibly in a liquid phase, can readily pass through the heater assembly.

Embodiments of the invention will now be described, by way of example only, with reference to the accompanying drawings, in which:

FIGS. 1*a* to 1*d* are schematic illustrations of a system, incorporating a cartridge, in accordance with an embodiment of the invention;

FIG. 2 is a schematic illustration of a clasp mechanism for the mouthpiece portion of the system of FIG. 1;

FIG. 3 is an exploded view of the cartridge of FIGS. 1*a* to 1*d;*

FIG. 4 is an exploded view of an alternative cartridge for use in a system as shown in FIGS. 1*a* to 1*d;*

FIG. 5*a* is a perspective underside view of the cartridge of FIG. 2;

FIG. 5*b* is a perspective topside view of the cartridge of FIG. 2, with the cover removed;

FIG. 6 is a detail view of a heater assembly used in the cartridge shown in FIG. 2;

FIG. 7 is a detail view of an alternative heater assembly that can be used in the cartridge shown in FIG. 2;

FIG. 8 is a detail view of a further alternative heater assembly that can be used in the cartridge shown in FIG. 2;

FIG. 9 is a detail view of a still further alternative heater assembly that can be used in the cartridge shown in FIG. 2;

FIG. 10 is a detail view of alternative mechanism for making electrical contact between the device and the heater assembly;

FIGS. 11*a* and 11*b* illustrate some cartridge housing shapes that can be used to ensure correct alignment of the cartridge in the device;

FIG. 12*a* is a detailed view of the filaments of the heater, showing a meniscus of liquid aerosol-forming substrate between the filaments;

FIG. 12*b* is a detailed view of the filaments of the heater, showing a meniscus of liquid aerosol-forming substrate between the filaments and a capillary material extending between the filaments;

FIGS. 13*a*, 13*b* and 13*c* illustrate alternative methods of manufacture for a heater assembly in accordance with the invention; and FIG. 14 illustrates an alternative design for a liquid storage portion incorporating a heater assembly.

FIGS. 15*a* and 15*b* illustrate additional alternative embodiments of a liquid storage portion incorporating a heater assembly.

FIG. 16 illustrates an alternative embodiment of the airflow and cartridge orientation with the aerosol-generating device.

FIG. 17 shows a cross-section of a cartridge system with high retention material and air passage through the HRM;

FIG. 18 shows a cross-section of another cartridge system with high retention material and air passage through the cartridge;

FIG. 19 shows an exploded view of the cartridge system of FIG. 18;

FIG. 20 shows a cross-section of a cartridge system with a liquid and air passage through the liquid.

FIGS. 1*a* to 1*d* are schematic illustrations of an aerosol-generating system, including a cartridge in accordance with an embodiment of the invention. FIG. 1*a* is a schematic view of an aerosol-generating device 10 and a separate cartridge 20, which together form the aerosol-generating system. In this example, the aerosol-generating system is an electrically operated smoking system.

The cartridge 20 contains an aerosol-forming substrate and is configured to be received in a cavity 18 within the device. Cartridge 20 should be replaceable by a user when the aerosol-forming substrate provided in the cartridge is depleted. FIG. 1*a* shows the cartridge 20 just prior to insertion into the device, with the arrow 1 in FIG. 1*a* indicating the direction of insertion of the cartridge.

The aerosol-generating device 10 is portable and has a size comparable to a conventional cigar or cigarette. The device 10 comprises a main body 11 and a mouthpiece portion 12. The main body 11 contains a battery 14, such as a lithium iron phosphate battery, control electronics 16 and a cavity 18. The mouthpiece portion 12 is connected to the main body 11 by a hinged connection 21 and can move between an open position as shown in FIG. 1 and a closed position as shown in FIG. 1*d*. The mouthpiece portion 12 is placed in the open position to allow for insertion and removal of cartridges 20 and is placed in the closed position when the system is to be used to generate aerosol, as will be described. The mouthpiece portion comprises a plurality of air inlets 13 and an outlet 15. In use, a user sucks or puffs on the outlet to draw air from the air inlets 13, through the mouthpiece portion to the outlet 15, and thereafter into the mouth or lungs of the user. Internal baffles 17 are provided to force the air flowing through the mouthpiece portion 12 past the cartridge, as will be described.

The cavity 18 has a circular cross-section and is sized to receive a housing 24 of the cartridge 20. Electrical connectors 19 are provided at the sides of the cavity 18 to provide an electrical connection between the control electronics 16 and battery 14 and corresponding electrical contacts on the cartridge 20.

Figures 1A, 1B:
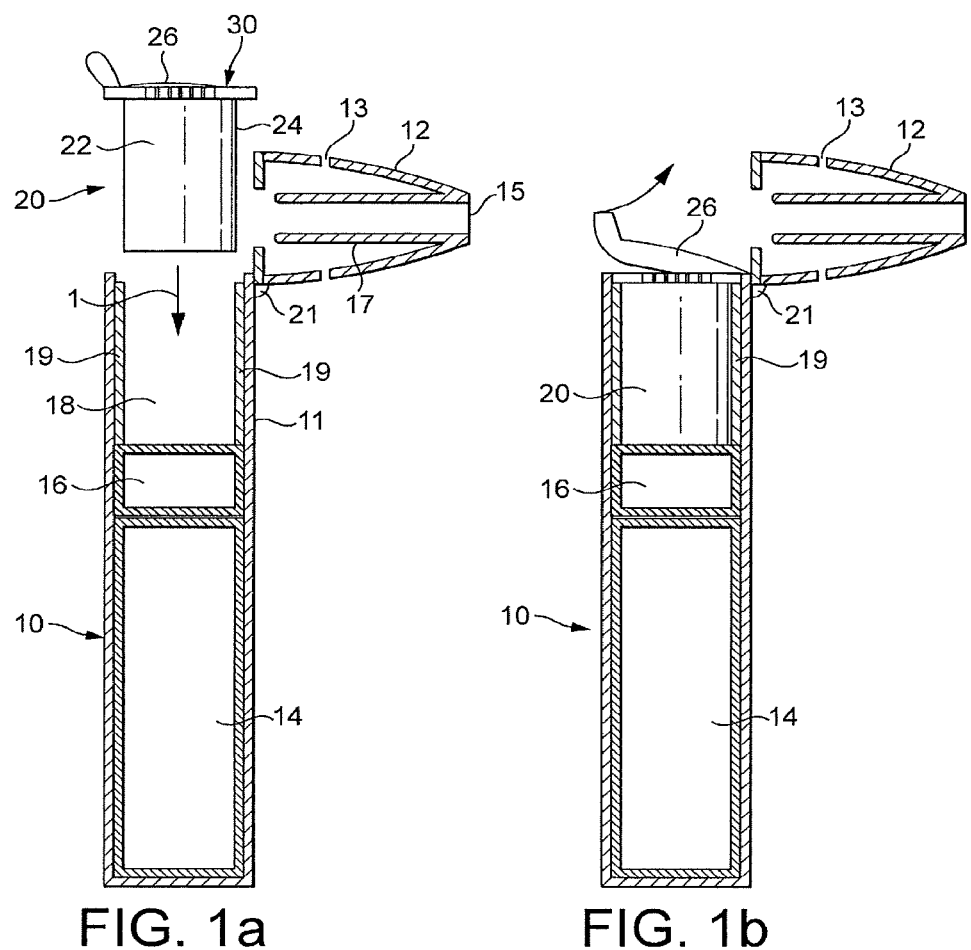
FIG. 1b shows the system of FIG. 1a with the cartridge inserted into the cavity 18, and the cover 26 being removed. In this position, the electrical connectors rest against the electrical contacts on the cartridge, as will be described.
Figures 1C, 1D:
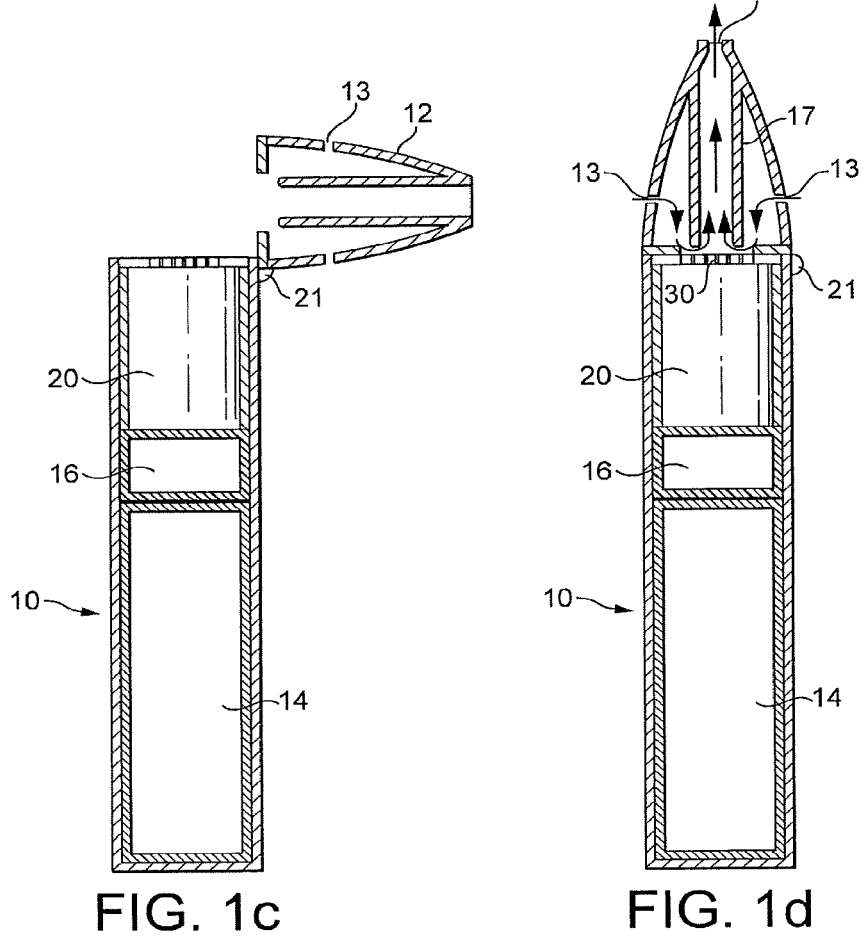
FIG. 1c shows the system of FIG. 1b with the cover 26 fully removed and the mouthpiece portion 12 being moved to a closed position.
Figure 2:
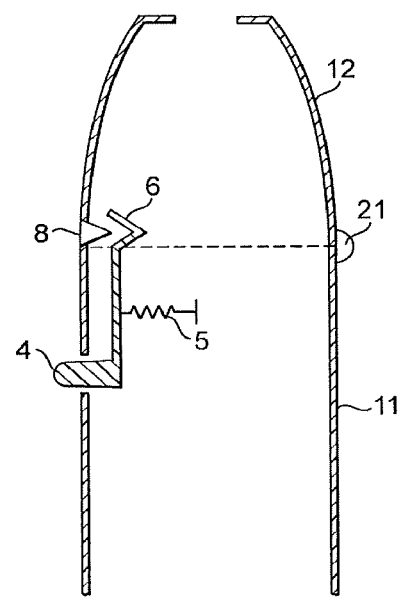

FIG. 1d shows the system of FIG. 1c with the mouthpiece portion 12 in the closed position. The mouthpiece portion 12 is retained in the closed position by a clasp mechanism, as is schematically illustrated in FIG. 2. FIG. 2 illustrates the main body 11 and mouthpiece portion 12 connected by hinged connection 21. The mouthpiece portion 12 comprises an inwardly extending tooth 8. When the mouthpiece portion is in a closed position, the tooth 8 engages a clasp 6 on the main body of the device. The clasp 6 is biased by biasing spring 5 to engage the tooth 8. A button 4 is fixed to the clasp 6. Button 4 can be depressed by a user against the action of the biasing spring 5 to release the tooth 8 from the clasp 6, allowing the mouthpiece portion to move to an open position. It will now be apparent to a person of ordinary skill in the art that other suitable mechanisms for retaining the mouthpiece in a closed position may be used, such as a snap fitting or a magnetic closure.

The mouthpiece portion 12 in a closed position retains the cartridge in electrical contact with the electrical connectors 19 so that a good electrical connection is maintained in use, whatever the orientation of the system is. The mouthpiece portion 12 may include an annular elastomeric element that engages a surface of the cartridge and is compressed between a rigid mouthpiece housing element and the cartridge when the mouthpiece portion 12 is in the closed position. This ensures that a good electrical connection is maintained despite manufacturing tolerances.

Of course other mechanisms for maintaining a good electrical connection between the cartridge and the device may, alternatively or in addition, be employed. For example, the housing 24 of the cartridge 20 may be provided with a thread or groove (not illustrated) that engages a corresponding groove or thread (not illustrated) formed in the wall of the cavity 18. A threaded engagement between the cartridge and device can be used to ensure the correct rotational alignment as well as retaining the cartridge in the cavity and ensuring a good electrical connection. The threaded connection may extend for only half a turn or less of the cartridge, or may extend for several turns. Alternatively, or in addition, the electrical connectors 19 may be biased into contact with the contacts on the cartridge, as will be described with reference to FIG. 8.

Figure 3:
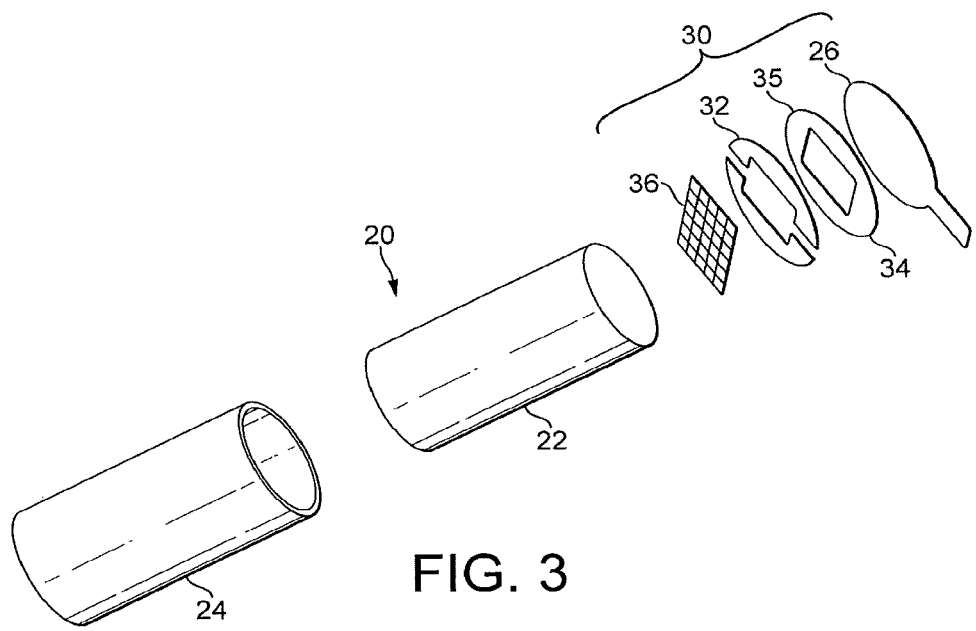

FIG. 3 is an exploded view of the cartridge 20. The cartridge 20 comprises a generally circular cylindrical housing 24 that has a size and shape selected to be received into the cavity 18. The housing contains a capillary material 22 that is soaked in a liquid aerosol-forming substrate. In this example the aerosol-forming substrate comprises 39% by weight glycerine, 39% by weight propylene glycol, 20% by weight water and flavourings, and 2% by weight nicotine. A capillary material is a material that actively conveys liquid from one end to another, and may be made from any suitable material. In this example the capillary material is formed from polyester.

The housing has an open end to which a heater assembly 30 is fixed. The heater assembly 30 comprises a substrate 34 having an aperture 35 formed in it, a pair of electrical contacts 32 fixed to the substrate and separated from each other by a gap 33, and a plurality of electrically conductive heater filaments 36 spanning the aperture and fixed to the electrical contacts on opposite sides of the aperture 35.

The heater assembly 30 is covered by a removable cover 26. The cover comprises a liquid impermeable plastic sheet that is glued to the heater assembly but which can be easily peeled off. A tab is provided on the side of the cover to allow a user to grasp the cover when peeling it off. It will now be apparent to one of ordinary skill in the art that although gluing is described as the method to a secure the impermeable plastic sheet to the heater assembly, other methods familiar to those in the art may also be used including heat sealing or ultrasonic welding, so long as the cover may easily be removed by a consumer.

Figure 4:
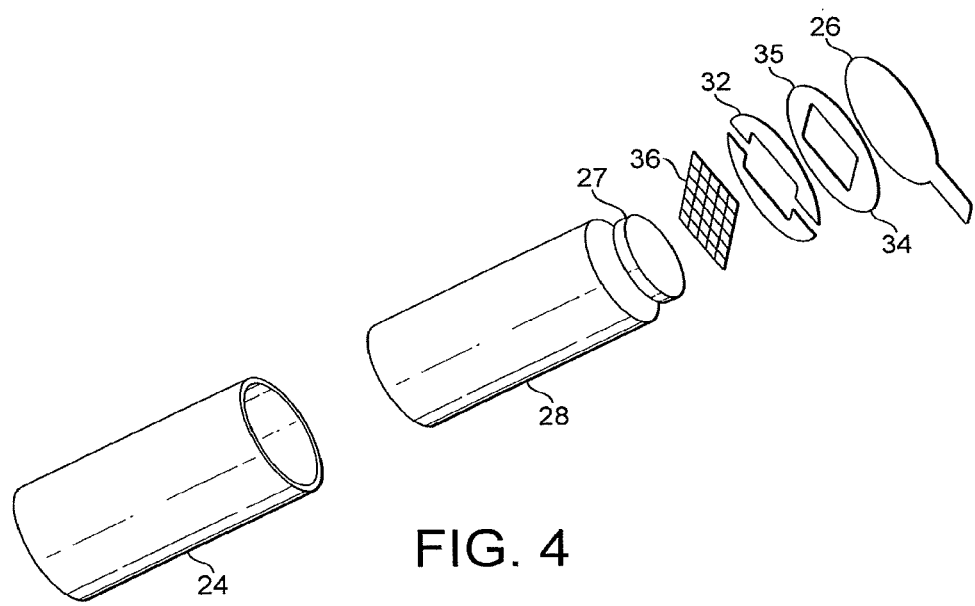

FIG. 4 is an exploded view of an alternative exemplary cartridge. The cartridge of FIG. 4 is the same size and shape as the cartridge of FIG. 3 and has the same housing and heater assembly. However, the capillary material within the cartridge of FIG. 4 is different to that of FIG. 3. There are two separate capillary materials 27, 28 in the cartridge of FIG. 4. A disc of a first capillary material 27 is provided to contact the heater element 36, 32 in use. A larger body of a second capillary material 28 is provided on an opposite side of the first capillary material 27 to the heater assembly. Both the first capillary material and the second capillary material retain liquid aerosol-forming substrate. The first capillary material 27, which contacts the heater element, has a higher thermal decomposition temperature (at least 160° C. or higher such as approximately 250° C.) than the second capillary material 28. The first capillary material 27 effectively acts as a spacer separating the heater element 36, 32 from the second capillary material 28 so that the second capillary material is not exposed to temperatures above its thermal decomposition temperature. The thermal gradient across the first capillary material is such that the second capillary material is exposed to temperatures below its thermal decomposition temperature. The second capillary material 28 may be chosen to have superior wicking performance to the first capillary material 27, may retain more liquid per unit volume than the first capillary material and may be less expensive than the first capillary material. In this example the first capillary material is a heat resistant material, such as a fiberglass or fiberglass containing material and the second capillary material is a polymer such as suitable capillary material. Exemplary suitable capillary materials include the capillary materials discussed herein and in alternative embodiments may include high density polyethylene (HDPE), or polyethylene terephthalate (PET).

Figure 5A:
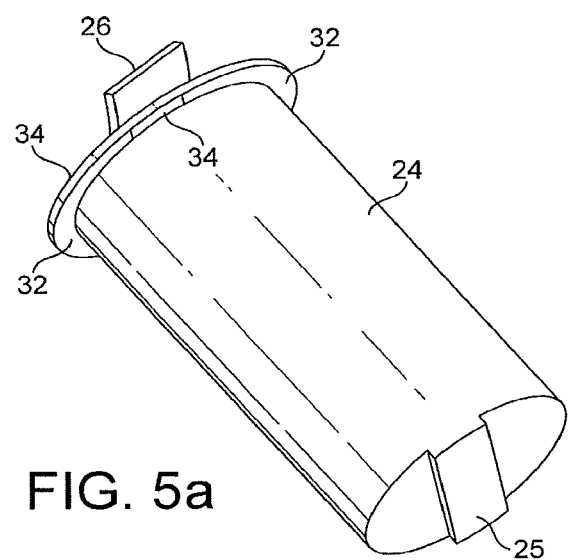

FIG. 5a is a perspective underside view of the cartridge of FIG. 3. It can be seen from FIG. 5a that the heater assembly extends in a lateral plane and extends laterally beyond the housing 24 so that the heater assembly forms a lip around the top of the housing 24. Exposed portions of the electrical contacts 32 face in an insertion direction of the cartridge so that when the cartridge is fully inserted into the cavity 18, the exposed portions of the contacts 32 contact the electrical connectors 19. The tab, provided on the side of the cover 26 to allow a user to grasp the cover when peeling it off, can be clearly seen. FIG. 5a also illustrates a locating portion 25 formed on the base of the cartridge for ensuring the correct orientation of the cartridge in the cavity of the device. The locating portion 25 is part of the injection moulded housing 24 and is configured to be received in a corresponding slot (not illustrated) in the base of the cavity 18. When the locating portion 25 is received in the slot in the cavity, the contacts 32 are aligned with the connectors 19.

Figure 5B:
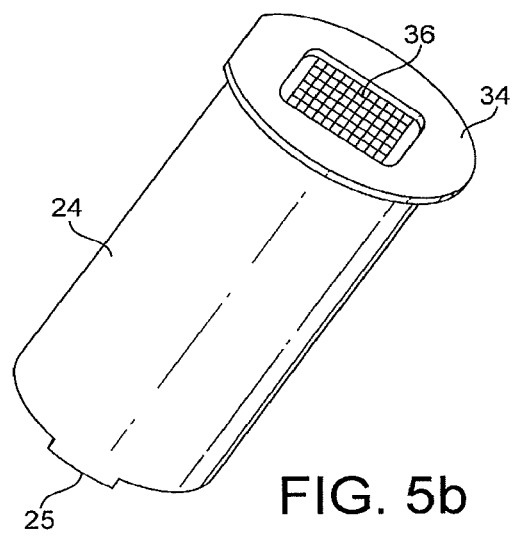

FIG. 5b is a perspective topside view of the cartridge of FIG. 3, with the cover removed. The heater filaments 36 are exposed through the aperture 35 in the substrate 34 so that vapourised aerosol-forming substrate can escape into the air flow past the heater assembly.

The housing 24 is formed from a thermoplastic, such as polypropylene. The heater assembly 30 is glued to the housing 24 in this example. However, there are several possible ways in which to assembly and fill the cartridge.

The cartridge housing may be formed by injection moulding. The capillary materials 22, 27, 28 may be formed by cutting suitable lengths of capillary material from a long rod of capillary fibres. The heater assembly may be assembled using a process as described with reference to FIGS. 11a, 11b and 11c. In one embodiment the cartridge is assembled by first inserting the one or more capillary materials 22, 27, 28 into the housing 24. A predetermined volume of liquid aerosol-forming substrate is then introduced into the housing 24, soaking the capillary materials. The heater assembly 30 is then pushed onto the open end of the housing and fixed to the housing 24 by gluing, welding, heat sealing, ultrasonic welding, or other methods that will now be apparent to one of ordinary skill in the art. The temperature of the housing is preferably held below 160° C. during any sealing operation to prevent unwanted volatising of the aerosol-forming substrate. The capillary material may be cut to a length such that it extends out of the open end of the housing 24 until it is compressed by the heater assembly. This promotes transport of aerosol-forming substrate into the interstices of the heater element in use.

In another embodiment, instead of pressing the heater assembly 30 onto the housing 24 and then sealing, the heater assembly and the open end of the housing may first be flash heated and then pressed together to bond the heater assembly 30 to the housing 24.

It is also possible to assemble the heater assembly 30 to the housing 24 before filling the housing with aerosol-forming substrate and subsequently to introduce the aerosol-forming substrate in to the housing 24. In that case, the heater assembly may be fixed to the cartridge using any of the methods described. The heater assembly or housing is then pierced using a hollow needle and the aerosol-forming substrate injected into the capillary material 22, 27, 28. Any opening made by the hollow needle is then sealed by heat sealing or by using a sealing tape.

Figure 6:
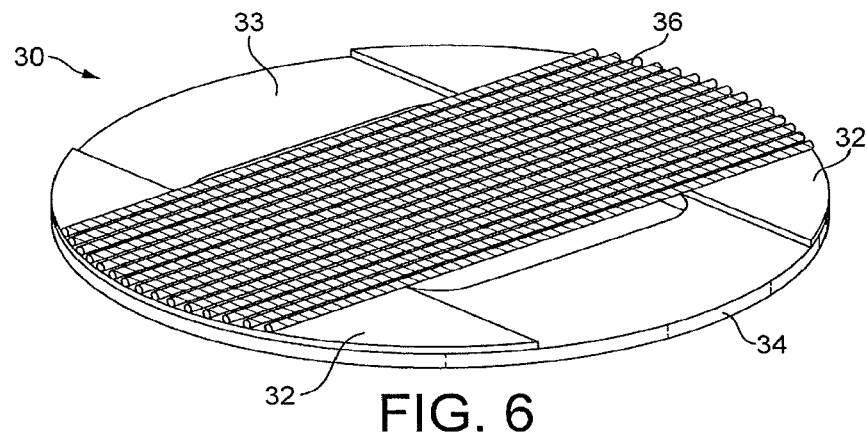

FIG. 6 is an illustration of a first heater assembly 30 in accordance with the disclosure. The heater assembly comprises a mesh formed from 304L stainless steel, with a mesh size of about 400 Mesh US (about 400 filaments per inch). The filaments have a diameter of around 16 µm. The mesh is connected to electrical contacts 32 that are separated from each other by a gap 33 and are formed from a copper foil having a thickness of around 30 µm. The electrical contacts 32 are provided on a polyimide substrate 34 having a thickness of about 120 µm. The filaments forming the mesh define interstices between the filaments. The interstices in this example have a width of around 37 µm, although larger or smaller interstices may be used. Using a mesh of these approximate dimensions allows a meniscus of aerosol-forming substrate to be formed in the interstices, and for the mesh of the heater assembly to draw aerosol-forming substrate by capillary action. The open area of the mesh, i.e. the ratio of the area of interstices to the total area of the mesh is advantageously between 25 and 56%. The total resistance of the heater assembly is around 1 Ohm. The mesh provides the vast majority of this resistance so that the majority of the heat is produced by the mesh. In this example the mesh has an electrical resistance more than 100 times higher than the electrical contacts 32.

The substrate 34 is electrically insulating and, in this example, is formed from a polyimide sheet having a thickness of about 120 µm. The substrate is circular and has a diameter of 8 mm. The mesh is rectangular and has side lengths of 5 mm and 2 mm. These dimensions allow for a complete system having a size and shape similar to a convention cigarette or cigar to be made. Another example of dimensions that have been found to be effective is a circular substrate of diameter 5 mm and a rectangular mesh of 1 mm×4 mm.

Figure 7:
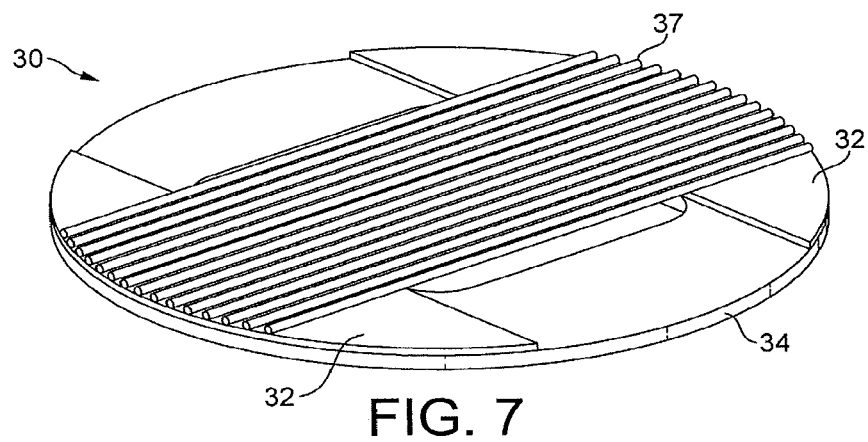

FIG. 7 is an illustration of an alternative, exemplary heater assembly in accordance with the disclosure. The heater assembly of FIG. 7 is the same as that shown in FIG. 6 but the mesh 36 is replaced by an array of parallel electrically conductive filaments 37. The array of filaments 37 are formed from 304L stainless steel and have a diameter of around 16 µm. The substrate 34 and copper contact 32 are as described with reference to FIG. 6.

Figure 8:
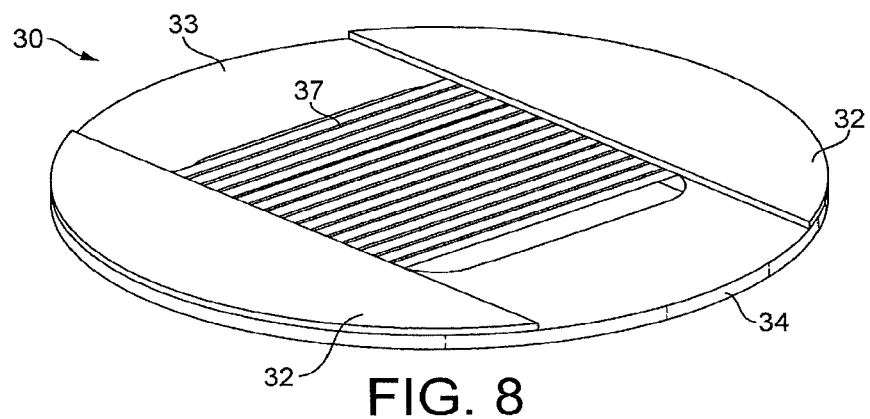

FIG. 8 is an illustration of another alternative heater assembly in accordance with the disclosure. The heater assembly of FIG. 8 is the same as that shown in FIG. 7 but in the assembly of FIG. 8, the filaments 37 are bonded directly to the substrate 34 and the contacts 32 are then bonded onto the filaments. The contacts 32 are separated from each other by insulating gap 33 as before, and are formed from copper foil of a thickness of around 30 µm. The same arrangement of substrate filaments and contacts can be used for a mesh type heater as shown in FIG. 6. Having the contacts as an outermost layer can be beneficial for providing reliable electrical contact with a power supply.

Figure 9:
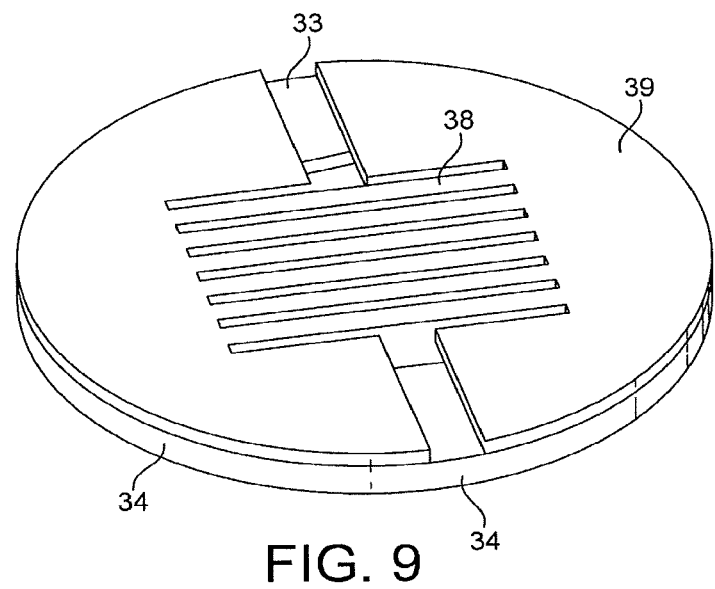

FIG. 9 is an illustration of an alternative heater assembly in accordance with the disclosure. The heater assembly of FIG. 9 comprises a plurality of heater filaments 38 that are integrally formed with electrical contacts 39. Both the filaments and the electrical contacts are formed from a stainless steel foil that is etched to define filaments 38. The contacts 39 are separated by a gap 33 except when joined by filaments 38. The stainless steel foil is provided on a polyimide substrate 34. Again the filaments 38 provide the vast majority of this resistance, so that the majority of the heat is produced by the filaments. In this example the filaments 38 have an electrical resistance more than 100 times higher than the electrical contacts 39.

Figure 10:
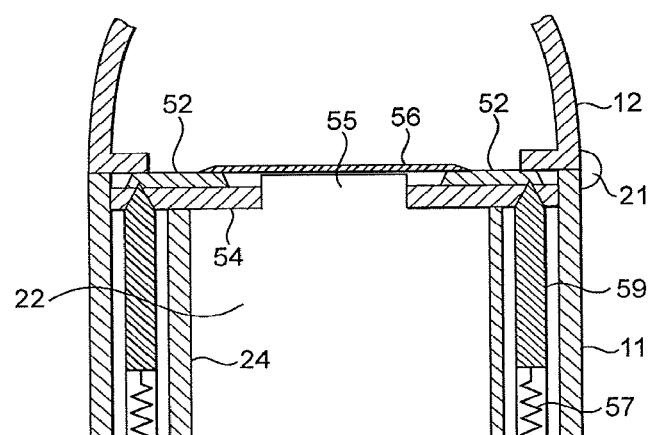

In the cartridge shown in FIGS. 3, 4 and 5, the contacts 32 and filaments 36, 38 are located between the substrate layer 34 and the housing 24. However, it is possible to mount the heater assembly to the cartridge housing the other way up, so that the polyimide substrate is directly adjacent to the housing 24. FIG. 10 illustrates an arrangement of this type. FIG. 10 shows a heater assembly comprising a stainless steel mesh 56, fixed to copper foil contacts 52. The copper contacts 52 are fixed to a polyimide substrate 54. An aperture 55 is formed in the polyimide substrate 54. The polyimide substrate is welded to the housing 24 of the cartridge. A capillary material 22, soaked in aerosol-forming substrate, fills the housing and extends through the aperture to contact the mesh 55. The cartridge is shown received in the main body 11 of the device and held between electrical connectors 59 and mouthpiece portion 12. In this embodiment, in order for the electrical connectors 59 to make an electrical connection with the contacts 52, the connectors 59 are adapted to pierce the polyimide substrate 54, as shown. The electrical connectors are made with sharpened ends and are urged into contact with the heater assembly by springs 57. The polyimide substrate may be pre-scored to ensure a good electrical contact is made, or may even be provided with apertures so that piercing of the substrate is not necessary. The springs 57 also ensure that a good electrical contact between the contacts 52 and the connectors 59 is maintained whatever the orientation of the system with respect to gravity.

Figure 11A:
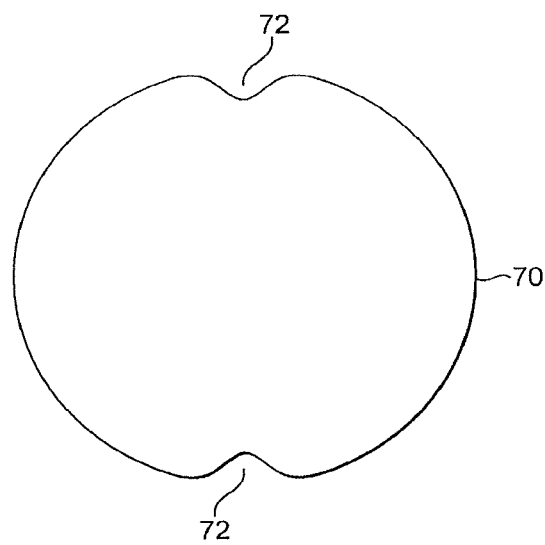
Figure 11B:
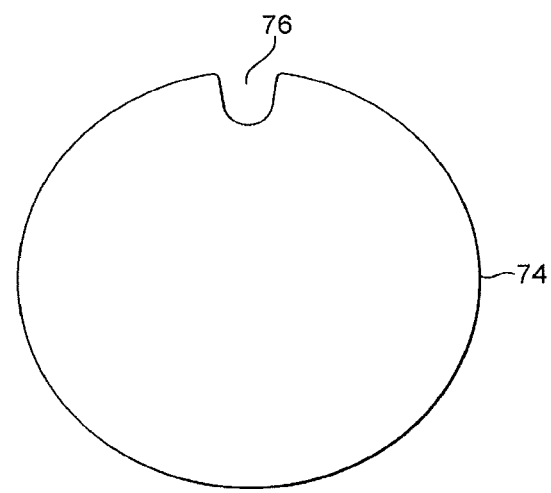

One means for ensuring the correct orientation of the cartridge 20 in the cavity 18 of the device has been described with reference to FIGS. 5a and 5b. The locating portion 25 can be formed as part of the moulded cartridge housing 24 to ensure the correct orientation. However, it will be apparent that other ways of ensuring the correct orientation of the cartridge are possible. In particular, if the housing is injection moulded, there are almost limitless possibilities for the shape of the cartridge. Once the desired internal volume of the cartridge has been chosen, the cartridge shape can be adapted to suit any cavity. FIG. 11a is a base view of one possible cartridge housing 70, allowing the cartridge to be oriented in two possible orientations. The cartridge housing 70 includes two symmetrically disposed, grooves 72. The grooves may extend partially or fully up the side of the housing 70. Corresponding ribs (not illustrated) may be formed on the walls of the cavity of the device, so that the cartridge can be received in the cavity in only two possible orientations. In the embodiment of FIG. 11a it is possible to have only a single rib in the cavity so that one of the grooves 72 is not filled by a rib and can be used as an air flow channel within the device. It is of course possible to restrict the cartridge to a single orientation within the cavity by providing only a single groove in the housing. This is illustrated in FIG. 11b, which shows a cartridge housing 74 with a single groove 76.

Although the embodiments described have cartridges with housings having a substantially circular cross section, it is of course possible to form cartridge housings with other shapes, such as rectangular cross section or triangular cross section. These housing shapes would ensure a desired orientation within the corresponding shaped cavity, to ensure the electrical connection between the device and the cartridge.

Figure 12A:
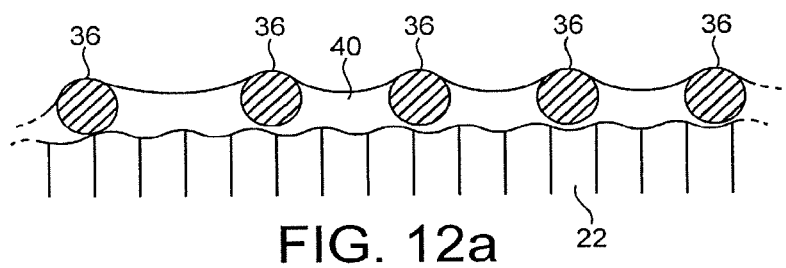
Figure 12B:
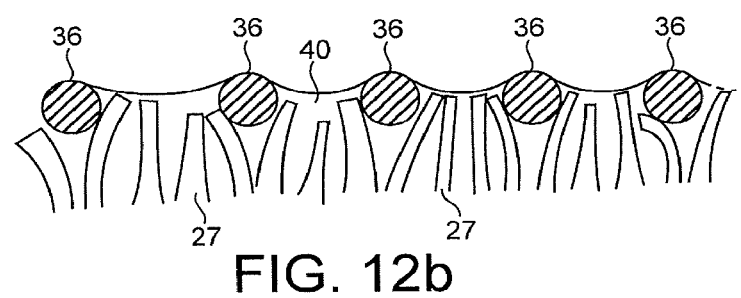

The capillary material 22 is advantageously oriented in the housing 24 to convey liquid to the heater assembly 30. When the cartridge is assembled, the heater filaments 36, 37, 38 may be in contact with the capillary material 22 and so aerosol-forming substrate can be conveyed directly to the mesh heater. FIG. 12a is a detailed view of the filaments 36 of the heater assembly, showing a meniscus 40 of liquid aerosol-forming substrate between the heater filaments 36. It can be seen that aerosol-forming substrate contacts most of the surface of each filament so that most of the heat generated by the heater assembly passes directly into the aerosol-forming substrate. In contrast, in conventional wick and coil heater assemblies only a small fraction of the heater wire is in contact with the aerosol-forming substrate. FIG. 12*b* is a detailed view, similar to FIG. 12*a*, showing an example of a capillary material 27 that extends into the interstices between the filaments 36. The capillary material 27 is the first capillary material shown in FIG. 4. It can be seen that by providing a capillary material comprising fine threads of fibres that extend into the interstices between the filaments 36, transport of liquid to the filaments can be ensured.

In use the heater assembly operates by resistive heating. Current is passed through the filaments 36, 37 38, under the control of control electronics 16, to heat the filaments to within a desired temperature range. The mesh or array of filaments has a significantly higher electrical resistance than the electrical contacts 32 and electrical connectors 19 so that the high temperatures are localised to the filaments. The system may be configured to generate heat by providing electrical current to the heater assembly in response to a user puff or may be configured to generate heat continuously while the device is in an "on" state. Different materials for the filaments may be suitable for different systems. For example, in a continuously heated system, graphite filaments are suitable as they have a relatively low specific heat capacity and are compatible with low current heating. In a puff actuated system, in which heat is generated in short bursts using high current pulses, stainless steel filaments, having a high specific heat capacity may be more suitable.

In a puff actuated system, the device may include a puff sensor configured to detect when a user is drawing air through the mouthpiece portion. The puff sensor (not illustrated) is connected to the control electronics 16 and the control electronics 16 are configured to supply current to the heater assembly 30 only when it is determined that the user is puffing on the device. Any suitable air flow sensor may be used as a puff sensor, such as a microphone.

In a possible embodiment, changes in the resistivity of one or more of the filaments 36, 38 or of the heater element as a whole may be used to detect a change in the temperature of the heater element. This can be used to regulate the power supplied to the heater element to ensure that it remains within a desired temperature range. Sudden changes in temperature may also be used as a means to detect changes in air flow past the heater element resulting from a user puffing on the system. One or more of the filaments may be dedicated temperature sensors and may be formed from a material having a suitable temperature coefficient of resistance for that purpose, such as an iron aluminium alloy, Ni—Cr, platinum, tungsten or alloy wire.

The air flow through the mouthpiece portion when the system is used is illustrated in FIG. 1*d*. The mouthpiece portion includes internal baffles 17, which are integrally moulded with the external walls of the mouthpiece portion and ensure that, as air is drawn from the inlets 13 to the outlet 15, it flows over the heater assembly 30 on the cartridge where aerosol-forming substrate is being vapourised. As the air passes the heater assembly, vapourised substrate is entrained in the airflow and cools to form an aerosol before exiting the outlet 15. Accordingly, in use, the aerosol-forming substrate passes through the heater assembly by passing through the interstices between the filaments 36, 37, 38 as it is vapourised.

There are a number of possibilities for manufacture and for the materials of the heater assembly. FIG. 13*a* is a schematic illustration of a first method of manufacture of a heater assembly. A roll of polyimide film 80 is provided with an array of apertures 82 in it. The apertures 82 may be formed by stamping. Bands of copper foil 84 are plated onto the polyimide film 80 between the apertures. Ribbons of stainless steel mesh 86 are then clad onto the polyimide film 80 on top of the copper foil 84 and over the apertures 82 in a direction orthogonal to the bands of copper foil. Individual heater assemblies 30 can then be cut or stamped out around each aperture 82. Each heater assembly 30 includes a portion of copper foil on opposite sides of the aperture, forming electrical contacts, and a strip of stainless steel mesh spans the aperture from one portion of copper to the other, as shown in FIG. 6.

Figure 13A:
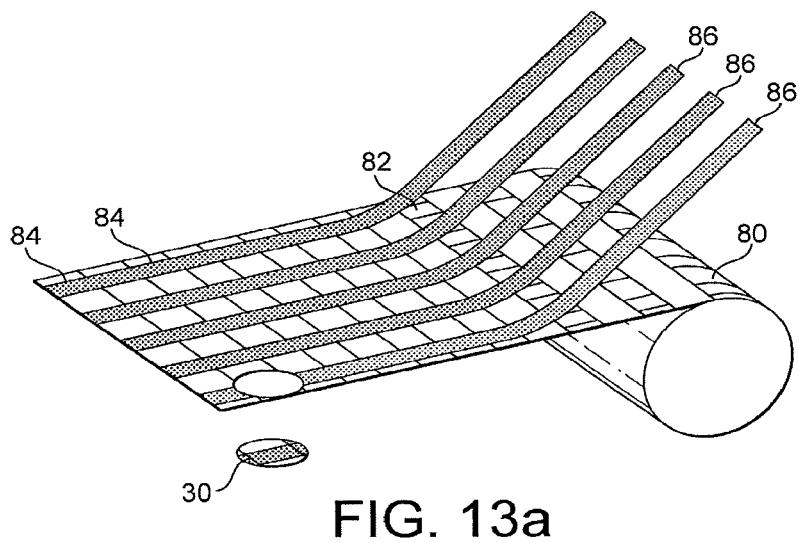
Figure 13B:
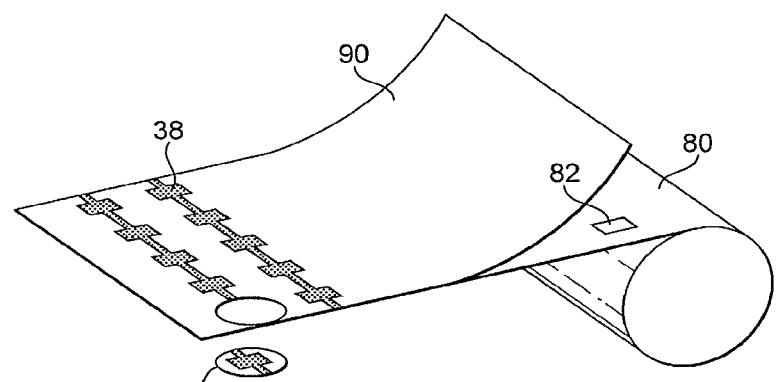

FIG. 13b illustrates another possible manufacturing process. In the process of FIG. 13b a polyimide film 80 of the type used in the process of FIG. 13a, is clad with stainless steel foil 90. The polyimide film 80 has an array of apertures 82 formed in it but these apertures are covered by the stainless steel foil 90. The foil 90 is then etched to define filaments 38 spanning the apertures 82 and separate contact portions on opposite sides of the apertures. Individual heater assemblies 92 can then be cut or stamped out around each aperture 82. This provides a heater assembly of the type shown in FIG. 9.

Figure 13C:
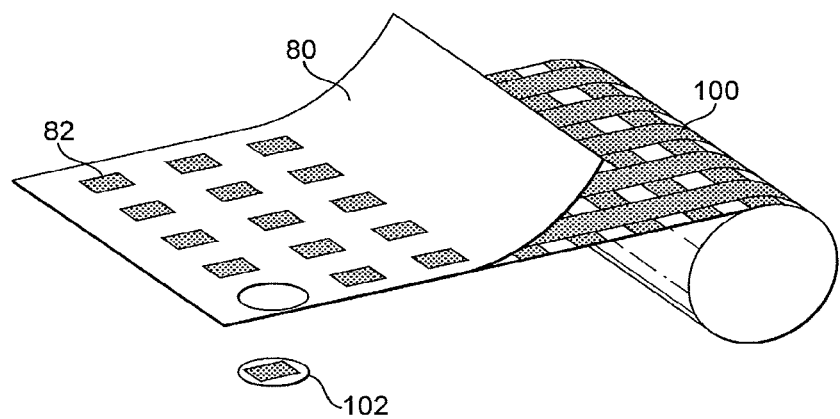

FIG. 13c illustrates a further alternative process. In the process of FIG. 13c a graphite based fabric 100 is first prepared. The graphite based fabric 100 comprises bands of electrically resistive fibres, suitable for use as heater filaments, adjacent bands of relatively non-conductive fibres. These bands of fibres are woven together with bands of relatively electrically conductive fibres that extend perpendicular to the resistive and non-conductive fibres. This fabric 100 is then bonded to a layer of polyimide film 80 of the type described with reference to FIGS. 13a and 13b, having an array of apertures 82. Individual heater assemblies 102 can then be cut or stamped out around each aperture. Each heater assembly 102 includes a portion of a band of conductive fibres on opposite sides of the aperture and a band of electrically resistive fibres span the aperture.

Figure 14:
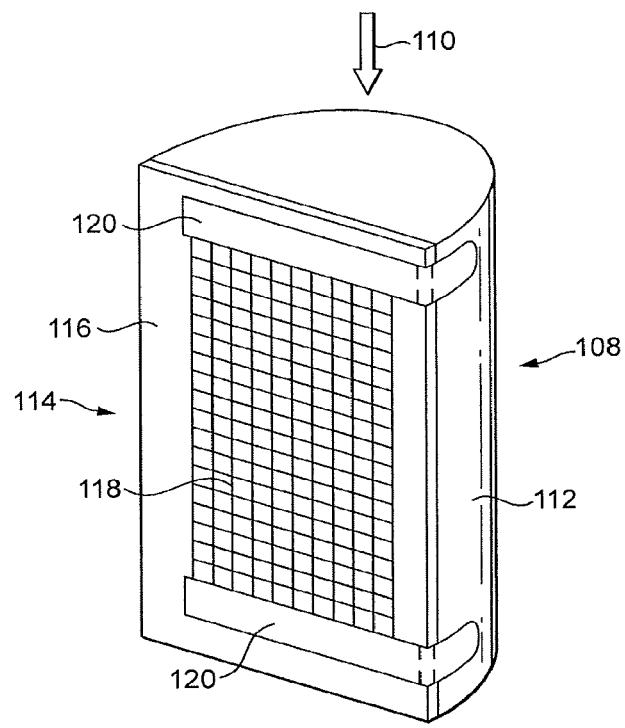

The cartridge design shown in FIGS. 5a and 5b has several advantages. However, alternative cartridge designs using the same type of heater assembly are possible. FIG. 14 illustrates an alternative cartridge design that is suited to a different pattern of airflow through the system. In the embodiment shown in FIG. 14, the cartridge 108 is configured to be inserted into the device in the direction indicated by the arrow 110. The cartridge 108 comprises a housing 112 which is shaped like a half cylinder and is open one side. A heater assembly 114 is provided across the open side and is glued or welded to the housing 112. The heater assembly 114 comprises an electrically insulating substrate 116, such as polyimide having an aperture formed in it. A heater element comprising a stainless steel mesh 118 and a pair of contact strips 120 is bonded to the electrically insulating substrate 116 and spans the aperture. The contact strips 120 are bent around the housing 112 to form contact pads on a curved surface of the housing. The electrical contact pads are configured to contact corresponding contacts (not illustrated) in the aerosol-generating device. The housing 112 is filled with a capillary material (not visible in FIG. 14) soaked in aerosol-forming substrate, as described with reference to the embodiment shown in FIGS. 1a to 1d.

The cartridge shown in FIG. 14 is configured for airflow past the heater assembly 114 in a direction opposite to arrow 110. Air is drawn into the system through an air inlet provided in a main body of the device and is sucked past the heater assembly 114, into a mouthpiece portion of the device (or cartridge) and into a user's mouth. Air drawn into the system may be directed, for example, in a direction parallel along mesh 118 by appropriate placement of air inlets.

Figure 15A:
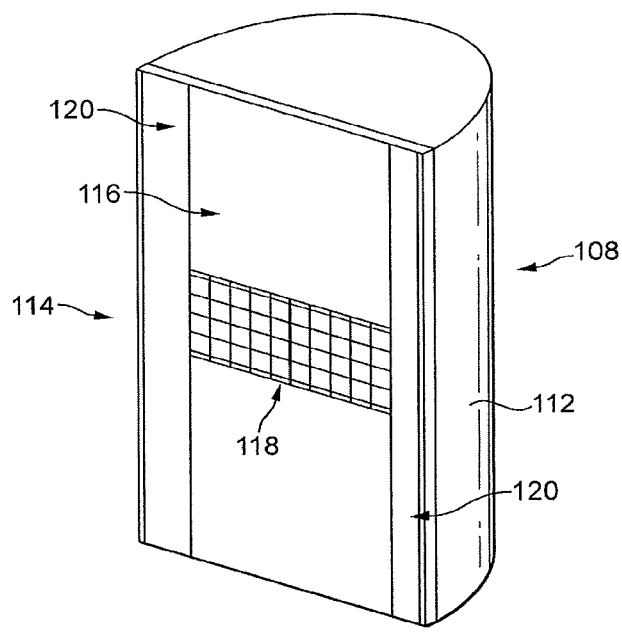
Figure 15B:
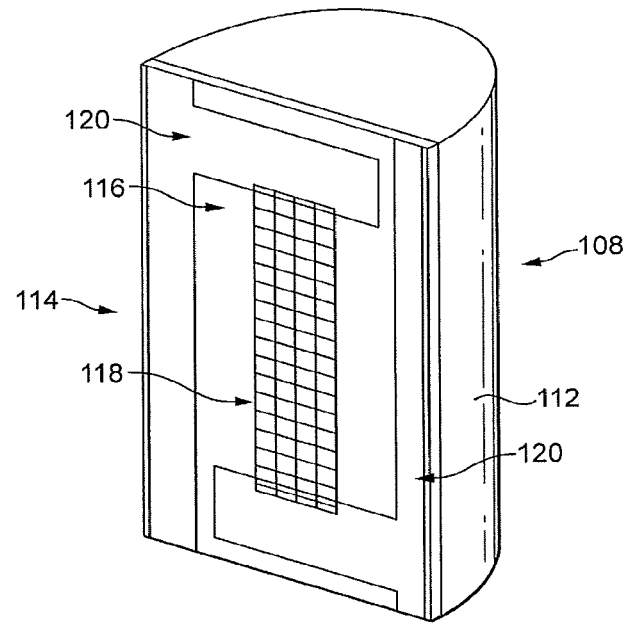

Alternative embodiments of the cartridge 108 are illustrated in FIGS. 15a and 15b. FIG. 15a further includes contract strips 120 spaced apart and running the length of the face having mesh 118. FIG. 15b further includes contacts 120 having roughly an L shape. Both cartridge designs illustrated in FIGS. 15a and 15b may be used to provide even larger contact areas to further ensure easy contact to contacts 19 if required. Strips 120 as illustrated in FIG. 15a may also configured to be slide into a contact 19 that is configured in a rail configuration (not illustrated) for receiving strips 120 to further position the cartridge. Such a rail-type configuration may advantageously provide a periodic cleaning of the contacts 19 as the insertion and removal of the cartridge will have a cleaning effect based on the friction of the contact sliding in and out of the rails.

Figure 16:
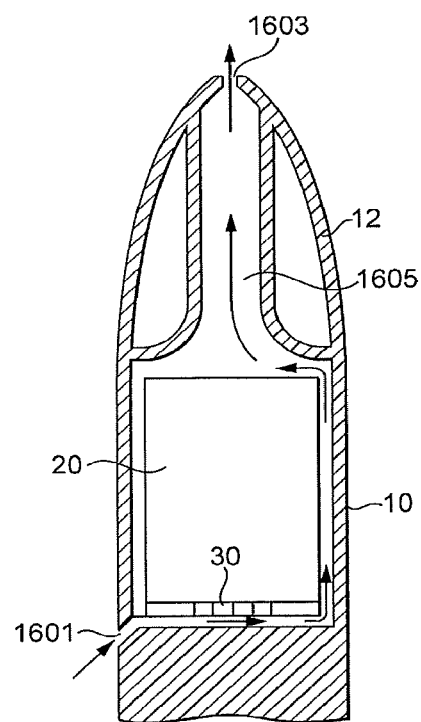

FIG. 16 illustrates yet another embodiment of an aerosol-generating system comprising a fluid-permeable electric heater assembly. FIG. 16 illustrates system where the heater assembly 30 is provided at an end of the cartridge 20 that is opposite to the mouthpiece portion 12. Airflow enters an air inlet 1601 and passes by the assembly and through an air outlet 1603 along a flow route 1605. Electrical contacts may be placed in any convenient location. Such a configuration is advantageous as it allows for shorter electrical connections within the system.

Other cartridge designs incorporating a heater assembly in accordance with this disclosure can now be conceived by one of ordinary skill in the art. For example, the cartridge may include a mouthpiece portion, may include more than one heater assembly and may have any desired shape. Furthermore, a heater assembly in accordance with the disclosure may be used in systems of other types to those already described, such as humidifiers, air fresheners, and other aerosol-generating systems The exemplary embodiments described above illustrate but are not limiting. In view of the above discussed exemplary embodiments, other embodiments consistent with the above exemplary embodiments will now be apparent to one of ordinary skill in the art.

Figure 17:
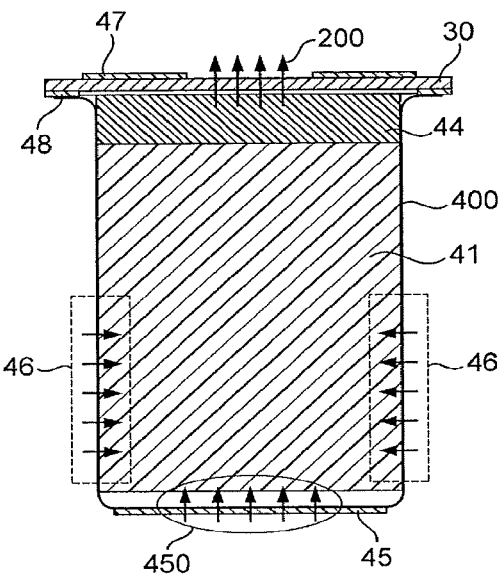

In FIG. 17 a cross section of a cartridge system, wherein a flow route comprises an airflow directed through the cartridge is illustrated. A fluid permeable heater, for example a mesh heater 30, comprises electrically conductive heater filaments 36 spanning the aperture of the housing 400. For sealing the top of the housing 400, a sealing layer 48, for example a polymer layer, is provided between the upper rim of the housing 400 and the heater 30. In addition, a sealing disc 47, for example a polymer disc, is provided on the top side of the heater 30. With the sealing disc 47 airflow through the heater may be controlled, in particular, airflow constraints may be provided. The sealing disc may also be arranged on the bottom side of the heater 30.

The cartridge housing 400 comprises a liquid containing capillary material such as a high retention material or high release material (HRM) 41 serving as liquid reservoir and directing liquid towards the heater 30 for evaporation at the heater. Another capillary material, a capillary disc 44, for example a fiber disc, is arranged between HRM 41 and heater 30. The material of the capillary disc 44 may be more heat resistant than the HRM 41 due to its closeness to the heater 30. The capillary disc is kept wet with the aerosol-forming liquid of the HRM to secure provision of liquid for vaporization if the heater is activated.

The housing 400 is provided with an air permeable bottom 45. The air permeable bottom is provided with an airflow inlet 450. The airflow inlet 450 allows air to flow through the bottom 45 into the housing in one and this direction only. No air or liquid may leave the housing through the air permeable bottom 45. The air permeable bottom 45 may for example comprise a semi-permeable membrane as airflow inlet 450 or may be a bottom cover comprising one or more one-way valves as will be shown below.

If low depression prevails on the side of the heater, as is the case during puffing, air may pass through the airflow inlet 450 into the cartridge. The airflow 200 will pass through the HRM 41 and through the heater 30. The aerosol containing airflow 200 will then flow to a downstream end of the aerosol generating device, preferably in a centrally arranged channel in a mouthpiece.

Side walls of the housing 400 may also be provided with lateral air permeable sections 46 for providing later airflows into the housing. Lateral air permeable sections 46 may be designed as the airflow inlets 450 in the air permeable bottom 45.

Figure 18:
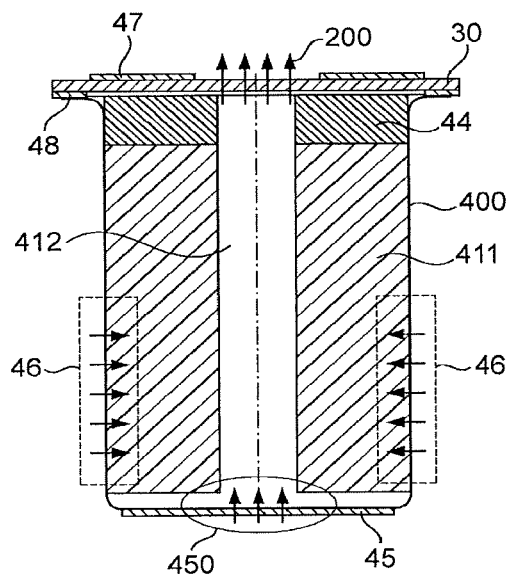

In FIG. 18 the arrangement and function of the cartridge system is basically the same as shown in FIG. 10. However, the HRM 41 is provided with a central opening 412. Air entering the airflow inlet 450 in the bottom 45 of the housing passes through the central opening 412. The airflow passes next to the HRM in the cartridge. With optional lateral air permeable sections 46 in the side wall of the housing 400, lateral airflow may be provided through the HRM 41.

Figure 19:
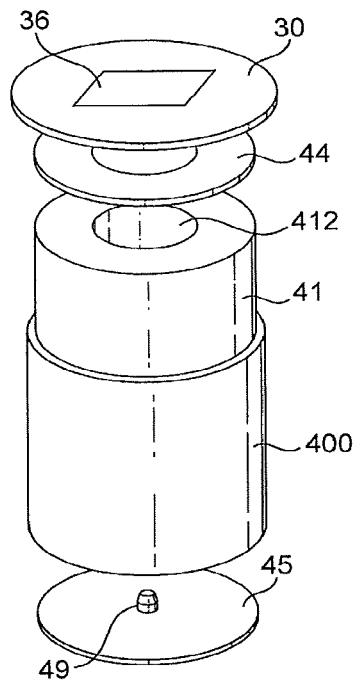

In FIG. 19 an exploded view of cartridge system as in FIG. 11 is shown. A ring-shaped tubular HRM 41 is provided in the housing 400. The bottom 45 of the housing is a disc comprising a one-way valve 49 arranged in the centre of the disc and aligned with the central opening 412 in the HRM 41. Such a one-way valve may for example be a commercially available valve, such as for example used in medical devices or in baby bottles.

Figure 20:
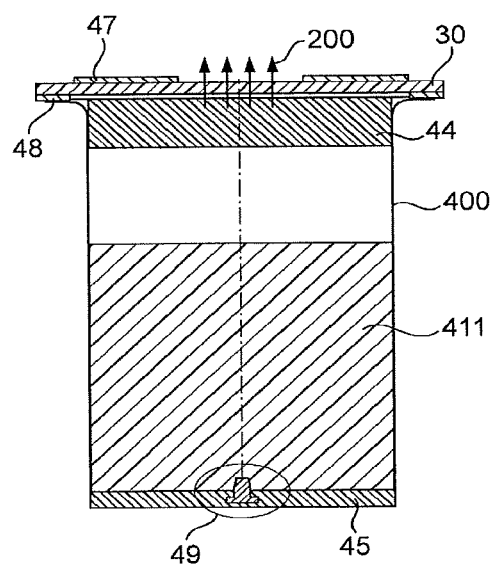

FIG. 20 is a cross section of another embodiment of a cartridge system. Same reference numerals are used for the same or similar elements. In this embodiment, the housing 400 is filled with an aerosol-forming liquid 411. The housing may be made of metal, plastics material, for example a polymeric material, or glass. The valve 49 may directly be moulded into the bottom 45 of the housing. The bottom 45 may also be provided with a cavity for air-tight assembly with the valve. Due to the valves preferably being made of a flexible material, tight assembly with the bottom material may be achieved.

In the above cartridge systems as described in FIGS. 17 to FIG. 20 the cartridge housing 400 may also be a separate cartridge container in addition to the cartridge housing as described for example in FIG. 1. Especially, a liquid 411 containing cartridge is a pre-manufactured product, which may be inserted into a cartridge housing provided in the aerosol generating system for receiving the pre-manufactured cartridge.

The invention claimed is:

1. A cartridge for an electrically operated aerosol-generating system, the cartridge comprising:
   a liquid storage portion comprising a housing holding a liquid aerosol-forming substrate, the housing having an opening; and
   a fluid-permeable heater assembly comprising a plurality of electrically conductive filaments, wherein the fluid-permeable heater assembly is fixed to the housing and extends across the opening of the housing.

2. The cartridge according to claim 1, wherein an area of the electrically conductive filaments is less than or equal to 25 mm$^2$.

3. The cartridge according to claim 1, wherein the fluid-permeable heater assembly is substantially flat.

4. The cartridge according to claim 3,
   further comprising a capillary medium,
   wherein the capillary medium is substantially a same size and shape as the fluid-permeable heater assembly, and the capillary medium is provided in contact with the fluid-permeable heater assembly, and
   wherein the liquid aerosol-forming substrate is drawn via the capillary medium to the electrically conductive filaments.

5. The cartridge according to claim 1, further comprising a mouthpiece portion.

6. The cartridge according to claim 1, wherein the housing of the liquid storage portion contains a capillary material configured to convey liquid aerosol-forming substrate to the heater assembly.

7. The cartridge according to claim 6, wherein the capillary material extends into interstices between the electrically conductive filaments.

8. The cartridge according to claim 6,
   wherein the capillary material includes a first capillary material and a second capillary material, the first capillary material being in contact with the heater assembly, and the second capillary material being in contact with the first capillary material and spaced apart from the heater assembly by the first capillary material, and
   wherein the first capillary material has a higher thermal decomposition temperature than the second capillary material.

9. The cartridge according to claim 8, wherein the second capillary material retains between 20 mg-160 mg of liquid.

10. The cartridge according to claim 9, wherein the thermal decomposition temperature of the first capillary material is at least 160° C.

11. The cartridge according to claim 9, wherein the thermal decomposition temperature of the first capillary material is at least 250° C.

12. The cartridge according to claim 1, wherein the fluid-permeable heater assembly further comprises an electrically insulating substrate on which the electrically conductive filaments are supported.

13. The cartridge according to claim 1, wherein the electrically conductive filaments extend across an aperture formed in the electrically insulating substrate.

14. The cartridge according to claim 13, wherein the capillary material is in contact with the electrically conductive filaments over substantially an entire extent of the aperture.

15. The cartridge according to claim 1, wherein the fluid-permeable heater assembly further comprises at least one filament made from a first material and at least one filament made from a second material different from the first material.

16. The cartridge according to claim 1, wherein the fluid-permeable heater assembly further comprises an electrically conductive contact in contact with a plurality of the electrically conductive filaments.

17. The cartridge according to claim 16, wherein the electrically conductive contact is integral with the plurality of the electrically conductive filaments.

18. The cartridge according to claim 16,
   wherein the fluid-permeable heater assembly extends in a lateral plane, and
   wherein the electrically conductive contact extends laterally beyond the housing of the liquid storage portion.

19. The cartridge according to claim 1, wherein the liquid storage portion is positioned on a first side of the electrically conductive filaments and an airflow channel is positioned on an opposite side of the electrically conductive filaments to the liquid storage portion, such that air flow past the electrically conductive filaments entrains vapourised liquid aerosol-forming substrate.

20. The cartridge according to claim 1,
wherein the housing comprises a cap and a tank,
wherein the cap closes the tank, and
wherein the cap is in close contact with the fluid-permeable heater assembly.

21. An aerosol-generating system, comprising a main unit and a cartridge according to claim 1, the cartridge being removably coupled to the main unit, wherein the main unit comprises a power supply.

22. The aerosol-generating system according to claim 21, further comprising electric circuitry connected to the fluid-permeable heater assembly and to an electrical power source, the electric circuitry being configured to monitor an electrical resistance of the fluid-permeable heater assembly or of one or more of the electrically conductive filaments of the fluid-permeable heater assembly, and to control a supply of power from the electrical power source to the fluid-permeable heater assembly dependent on the electrical resistance of the fluid-permeable heater assembly or the one or more electrically conductive filaments.

23. The aerosol-generating system according to claim 21, wherein the aerosol-generating system is an electrically operated smoking system.

24. A method of manufacture of a cartridge for an electrically operated aerosol-generating system, the method comprising:
providing a liquid storage portion comprising a housing having an opening;
filling the liquid storage portion with liquid aerosol-forming substrate; and
fixing a fluid-permeable heater assembly comprising a plurality of electrically conductive filaments to the liquid storage portion,
wherein the fluid-permeable heater assembly extends across the opening of the housing of the liquid storage portion.

* * * * *